United States Patent [19]

Cherry et al.

[11] E Re. 29,921

[45] Reissued Feb. 27, 1979

[54] ELECTROCARDIOGRAPHIC COMPUTER

[75] Inventors: Isaac R. Cherry, Mission Viejo; Donald L. Anderson, San Juan Capistrano, both of Calif.

[73] Assignee: Del Mar Avionics, Irvine, Calif.

[21] Appl. No.: 899,241

[22] Filed: Apr. 24, 1978

Related U.S. Patent Documents

Reissue of:

[64] Patent No.: 4,073,011
Issued: Feb. 7, 1978
Appl. No.: 717,651
Filed: Aug. 25, 1976

[51] Int. Cl.[2] ..... A61B 5/04; G06F 15/42

[52] U.S. Cl. ..... 364/900; 360/73; 360/74; 360/90; 128/2.06 G; 128/2.06 A

[58] Field of Search ... 364/200 MS File, 900 MS File; 128/2.06 A, 2.06 G, 2.06 B, 2.06 F, 2.06 R; 346/33 ME; 360/73, 73 R, 90; 179/100.15

[56] References Cited

U.S. PATENT DOCUMENTS

| | | | |
|---|---|---|---|
| T916,007 | 11/1973 | Bonner | 364/200 |
| 3,728,685 | 4/1973 | Stalnert | 364/900 |
| 3,810,102 | 5/1975 | Parks et al. | 364/200 |
| 3,815,100 | 6/1974 | Winchester et al. | 364/200 |
| 3,909,792 | 9/1975 | Harris et al. | 364/900 |
| 3,913,567 | 10/1975 | Streckmann | 128/2.06 G |
| 3,922,686 | 11/1975 | France et al. | 346/33 ME |
| 3,934,267 | 1/1976 | Kosaka et al. | 360/6 |
| 4,006,737 | 2/1977 | Cherry | 128/2.06 G |

*Primary Examiner*—Mark E. Nusbaum
*Attorney, Agent, or Firm*—Smyth, Pavitt, Siegemund, Jones & Martella

[57] ABSTRACT

A multi-speed ECG magnetic tape scanning device for processing and observing in a relatively short interval of time large quantities of ECG signals from two pairs of ECG leads. The ECG information is recorded on a miniature recorder which the patient carries to record the information for a long period of time, such as 24 hours. The recorder includes a built-in clock with a visible display. The recorder also includes an event marker, which is activated by the patient when the patient experiences an event. The play-back of the ECG information is in real time or at multiple high speed play-back speeds of 30, 60 and 120 times real time. During play-back at high speed, a multi-speed multi-channel paper writer reproduces analog trend data, digital printed data and event marking. The trend information is usually heart rate and ST segment level, so as to produce a scanning of an entire 24 hour information tape in as short a period as 12 minutes. The tape scanning device can run on trend to print out trend to the end of the tape, and then stop automatically. Alternatively, the tape scanning device can run on trend to the end of the tape and then automatically cycle to the beginning of the tape to print-out trend and periodically slow the tape down to real time for the print-out of predetermined events in real time. After each print-out in real time, the playback always goes back to the originally selected trend speed for the continuation of the trend print-out. Various short events may be used to slow the read-out to real time, such as an event marking on the tape which has been activated by the patient. Also, any preselected abnormalities in heart function such as abnormal VE's, SVE's, ST level, rapid heart beat, slow heart rate, etc., may be used to print-out in real time. An arrhythmia computer detects and digitally displays the number of premature ventricular contractions (VE) and superventricular ectopic beats (SVE) and actuates the event markers on a paper writer when the arrhythmia occurrences exceed a predetermined number of occurrences during a predetermined time interval. The event marking may also be used to control the slow down during trend read-out to print out the ECG signals in real time to show the arrhythmia occurrences. The arrhythmia computer includes the ability to select one or a number of parameters to determine the occurrence of an arrhythmia. These parameters may be paired beats, prematurity, width or amplitude.

54 Claims, 31 Drawing Figures

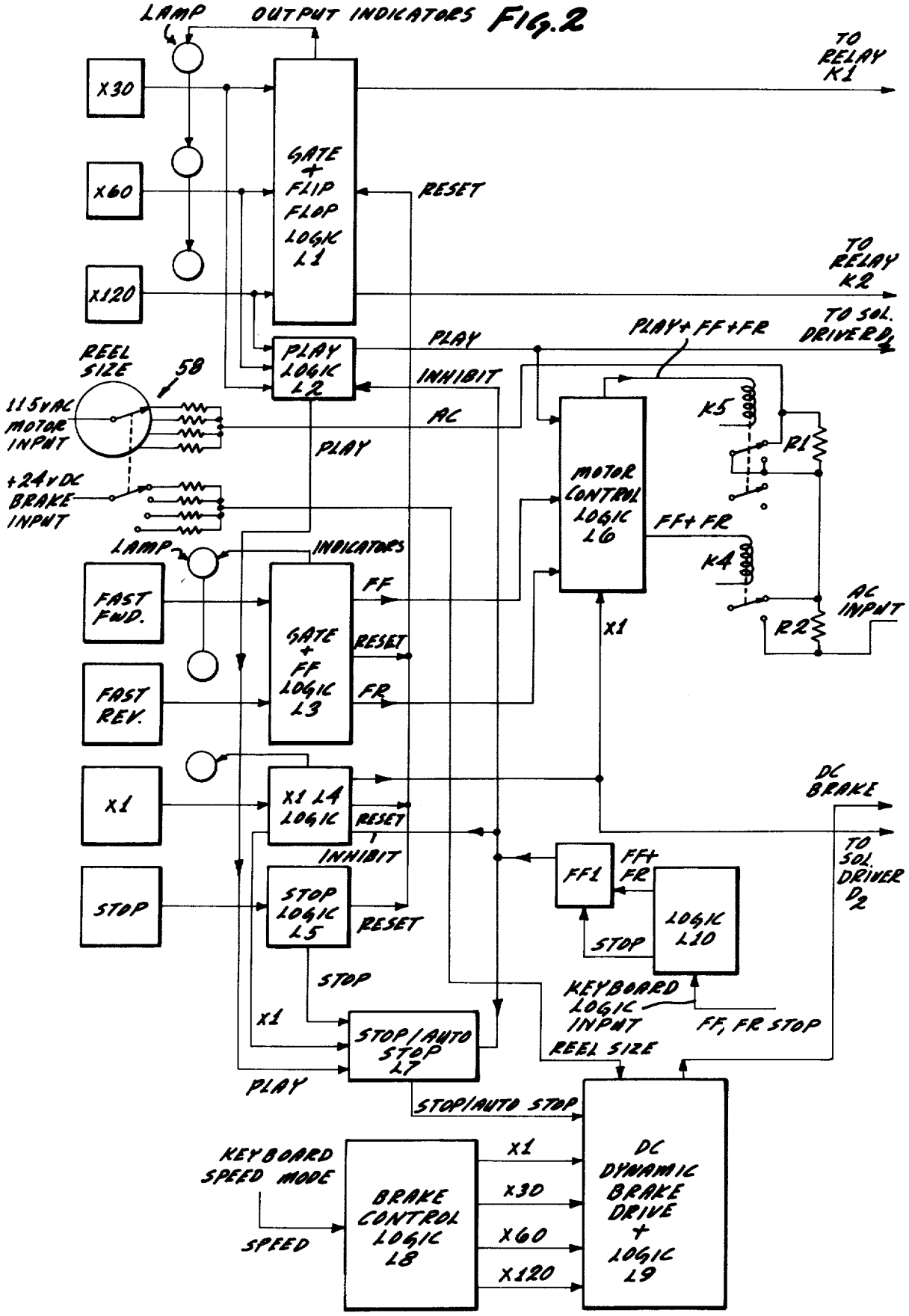
LAMP
OUTPUT INDICATORS
Fig. 2
X30
X60
X120
GATE + FLIP FLOP LOGIC L1
RESET
TO RELAY K1
TO RELAY K2
TO SOL. DRIVER D1
PLAY LOGIC L2
PLAY
INHIBIT
PLAY+FF+FR
REEL SIZE
58
115vAC MOTOR INPUT
AC
PLAY
+24vDC BRAKE INPUT
MOTOR CONTROL LOGIC L6
K5
R1
FF+FR
K4
R2
AC INPUT
LAMP
INDICATORS
FAST FWD.
FAST REV.
GATE + FF LOGIC L3
FF
RESET
FR
X1
X1 L4 LOGIC
RESET
INHIBIT
DC BRAKE
TO SOL. DRIVER D2
STOP
STOP LOGIC L5
RESET
FF1
FF+FR
LOGIC L10
STOP
STOP
KEYBOARD LOGIC INPUT
FF, FR STOP
X1
STOP/AUTO STOP L7
REEL SIZE
PLAY
STOP/AUTO STOP
KEYBOARD SPEED MODE
SPEED
BRAKE CONTROL LOGIC L8
X1
X30
X60
X120
DC DYNAMIC BRAKE DRIVE + LOGIC L9

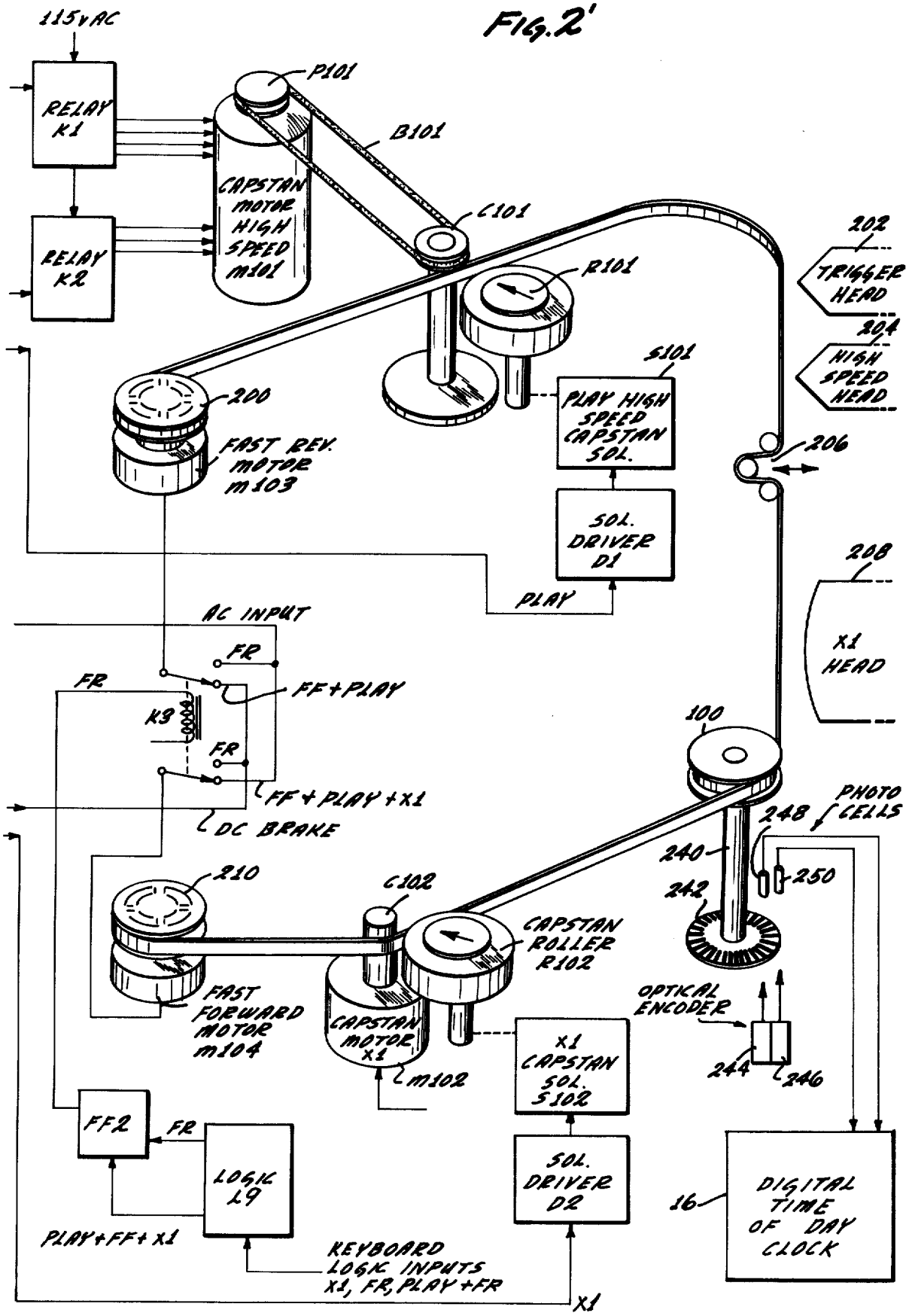
FIG. 2'
115vAC
RELAY K1
RELAY K2
P101
B101
CAPSTAN MOTOR HIGH SPEED M101
C101
R101
202
TRIGGER HEAD
204
HIGH SPEED HEAD
S101
PLAY HIGH SPEED CAPSTAN SOL.
200
FAST REV. MOTOR M103
206
SOL. DRIVER D1
PLAY
208
X1 HEAD
AC INPUT
FR
FF+PLAY
K3
FF+PLAY+X1
DC BRAKE
100
PHOTO CELLS
248
240
250
242
210
C102
CAPSTAN ROLLER R102
FAST FORWARD MOTOR M104
CAPSTAN MOTOR X1
M102
OPTICAL ENCODER
244
246
X1 CAPSTAN SOL. S102
SOL. DRIVER D2
FF2
LOGIC L9
PLAY+FF+X1
KEYBOARD LOGIC INPUTS X1, FR, PLAY+FR
16
DIGITAL TIME OF DAY CLOCK
X1

Fig. 2"
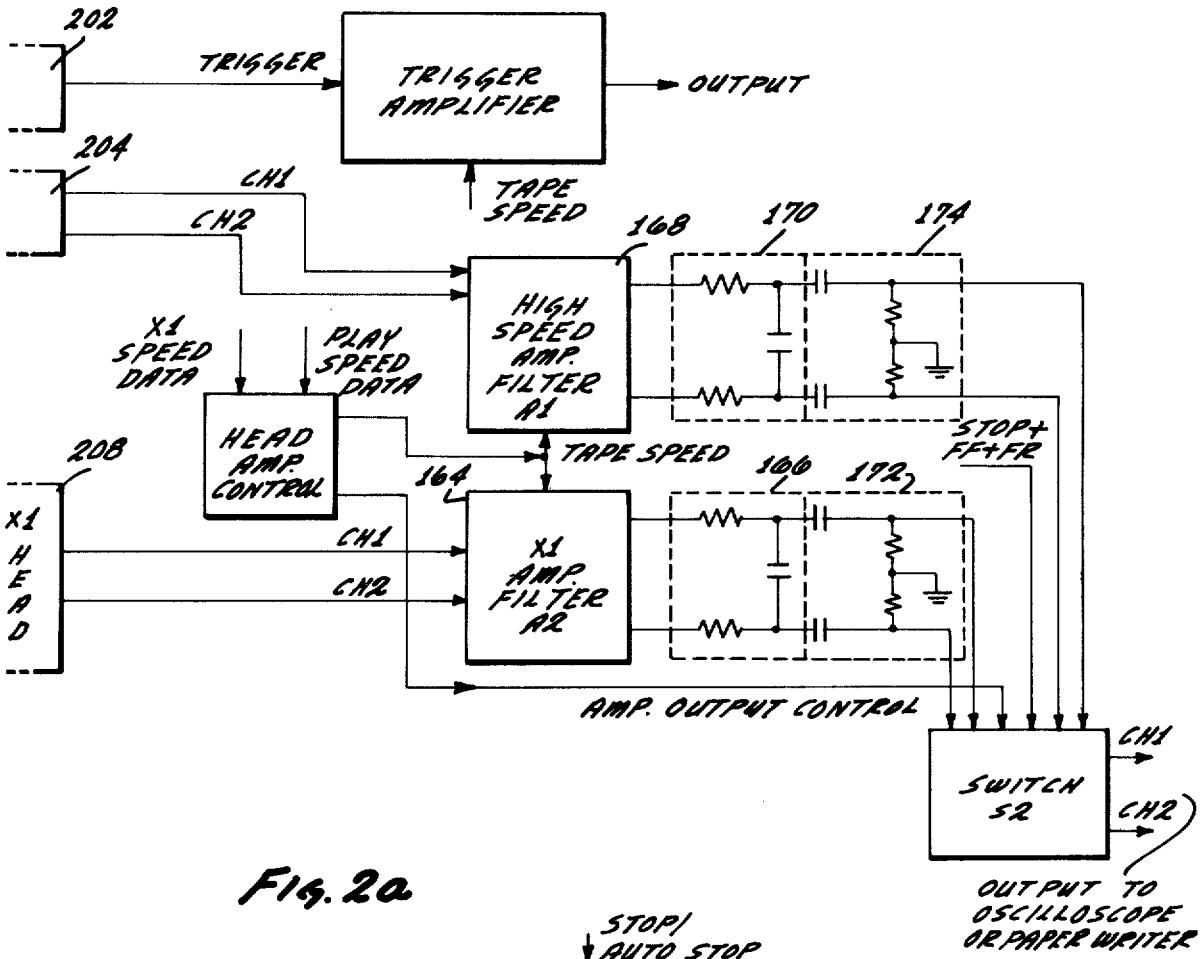
Fig. 2a
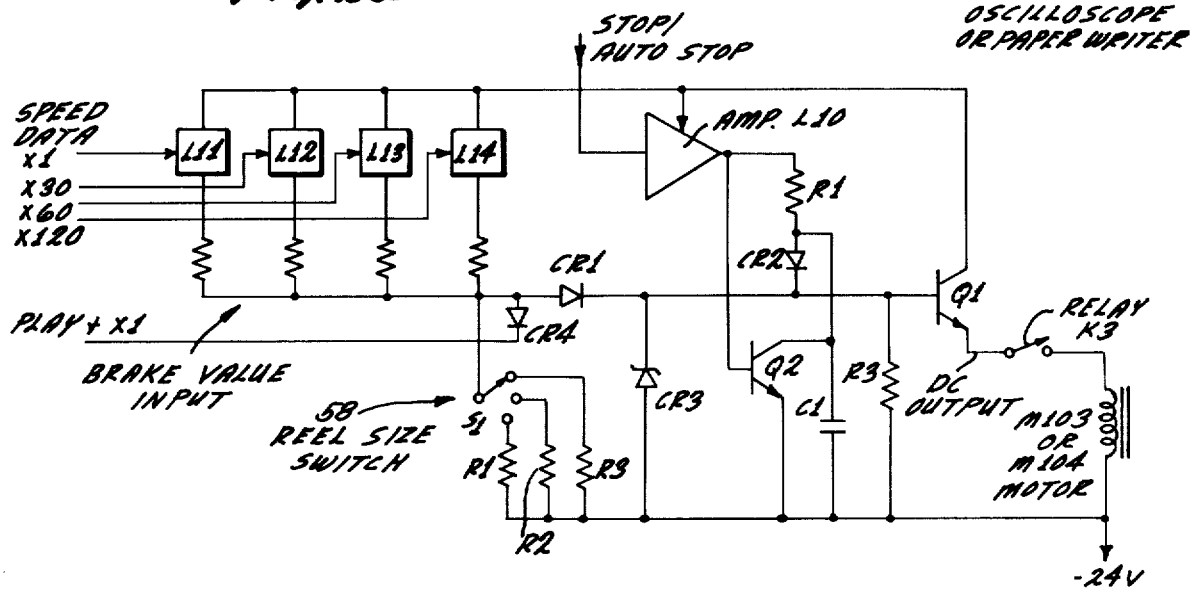

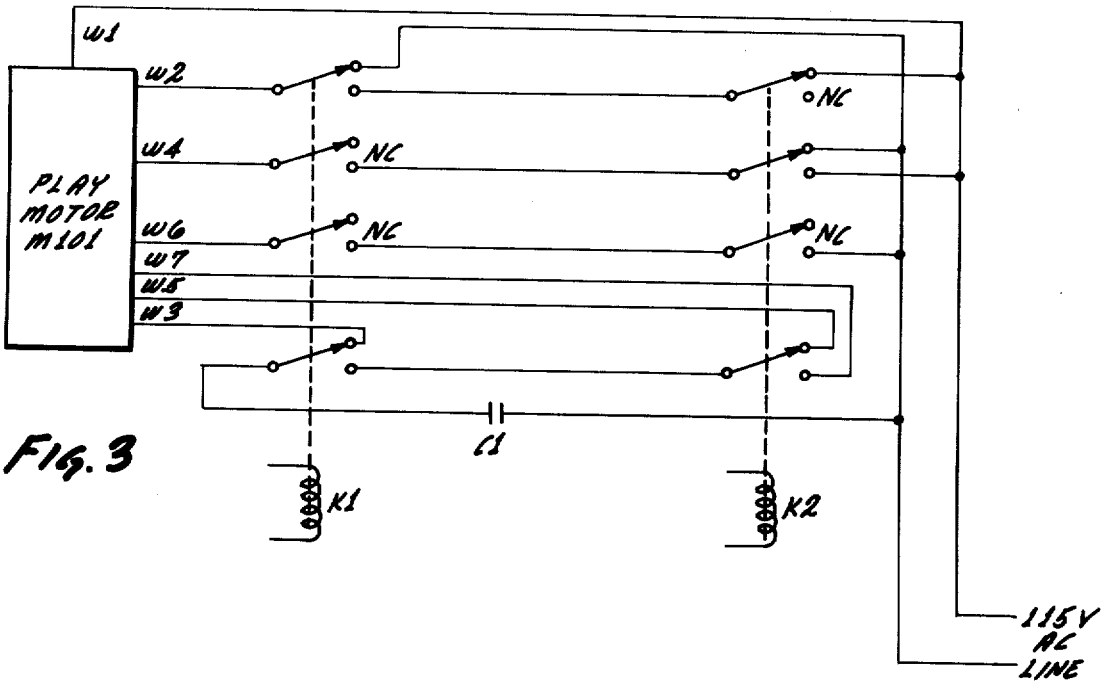
FIG. 3
FIG. 6
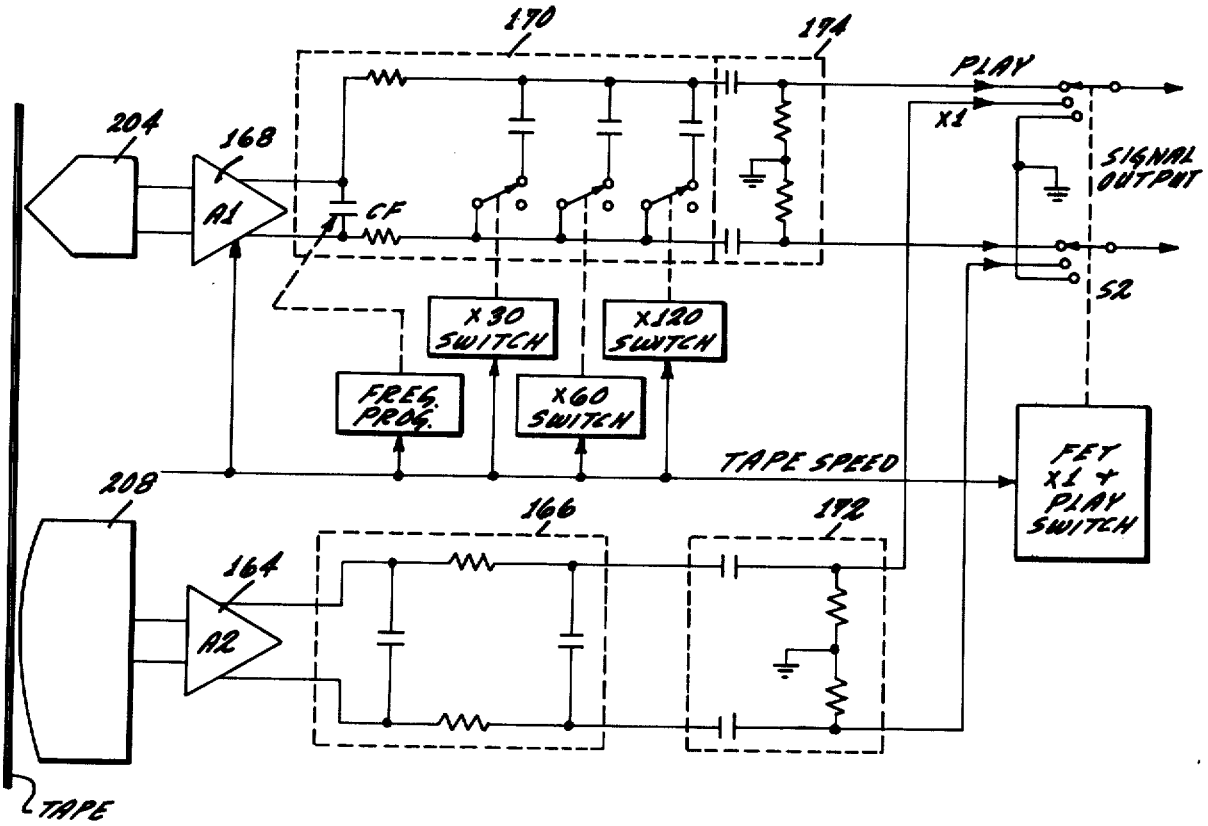

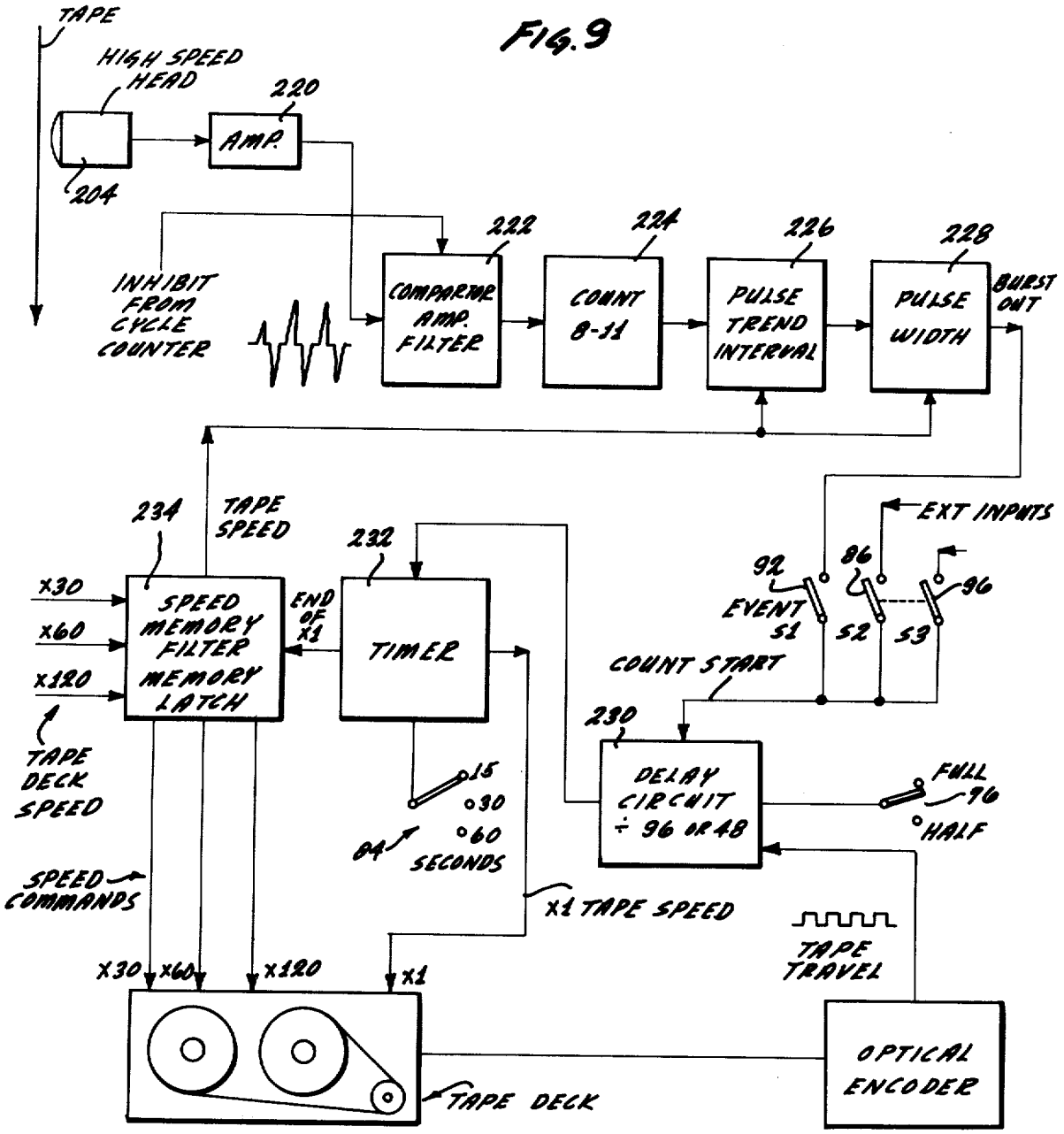
FIG. 9a
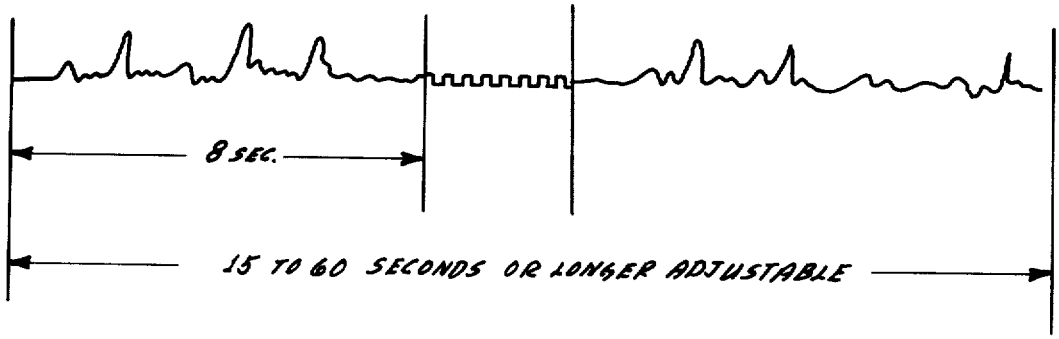

ELECTROCARDIOGRAPHIC COMPUTER

Matter enclosed in heavy brackets [ ] appears in the original patent but forms no part of this reissue specification; matter printed in italics indicates the additions made by reissue.

The present invention relates to an electrocardiographic computer with visual display and in particular, to a computer for automatically processing large volumes of electrocardiac signals and for displaying and permanently recording an analysis of these large volumes of signals in a relatively short period of time.

Electrical signals that circulate upon the surface of a person's skin as a result of the expansions and contractions of the cardiac muscle are known as ECG signals. These ECG electrical signals exhibit particular waveforms and the action of the cardiac muscle and the condition of the muscle produce waveforms with particular characteristic relationship. A well-known technique in the medical field is to place electrodes on the patient's skin so as to sense the ECG signals for visual presentation. Many types of devices are currently available to provide the visual presentation of the ECG signal for viewing either in real time or for viewing at some subsequent time by a cardiologist or other trained personnel.

For example, it is possible to use a cathode-ray oscilloscope to provide for the presentation of the ECG signal either directly from the patient in real time, or at a later time from a recording of the ECG signals using a recording device such as a magnetic tape recorder. In addition, the ECG signals may be recorded by a paper writer on paper tape which is called an electrocardiograph. The graph may be subsequently viewed by trained personnel for a determination of the characteristics of the waveforms. All of these above methods provide for a fairly limited analysis of the ECG signals since the signals are generally monitored for a relatively short period of time and do not provide for the monitoring of the characteristics of the ECG signals over a long period of time, which period of time should include the normal activities of the patient.

A more desirable method of analyzing ECG signals is to accumulate large volumes of such signals and with the accumulation of the signals occurring while the patient is engaged in his normal activities. Since it would be impossible to analyze such recorded signals on a one-to-one time relationship because of the long recording period, the subsequent presentation of the ECG signals must be at an accelerated rate. Electrocardioscanner ®type of analysis is accomplished by recording the ECG signals in real time on a small compact tape recorder which is worn by the patient who is instructed to engage in his normal activities. The recorded ECG signals are then processed by replaying the signals at a much faster speed and with a presentation of the ECG signals on a cathode-ray oscilloscope, and with each ECG complex superimposed on the predecessor complexes. This type of superimposed replay in fast time is known as an AVSEP® display and has been registered under the trademark AVSEP® and Electrocardioscammer ®. As a particular example of a system which may be used for the recording and playback of ECG signals with the recording in real time and with the playback in fast time, reference is made to U.S. Pat. No. 3,215,136, issued Nov. 2, 1965, in the name of Norman J. Holter, et al.

In the prior art ECG scanning device disclosed in U.S. Pat. Ser. No. 3,215,136, the superimposition of the ECG signals is accomplished by recording the same ECG signal on two different tracks of a magnetic recording tape, but with the same signals on the different tracks longitudinally displaced. The playback of the ECG signals is accomplished by using spaced magnetic playback heads for reproducing the ECG signals on the two tracks. A first one of these playback heads reproduces the ECG signals on a first one of the tape tracks for the purpose of producing a trigger signal while the second one of the playback heads reproduces the ECG signal on a visual indicator such as an oscilloscope.

The two playback heads reproduce the information which is longitudinally displaced on the two tracks so that the trigger signal which is generated from the first track synchronizes the horizontal sweep of the oscilloscope so that each ECG trace on the oscilloscope is initiated at the same point in the ECG complex. In this way each ECG trace is displayed in its entirety.

The prior art devices for providing the superimposed display as described above are capable of processing and providing a presentation of data from only one pair of ECG leads attached to the patient and these prior art devices are capable of high speed playback at only one speed. The prior art electrocardioscanning system such as shown in U.S. Pat. No. 3,215,136 have proven to be of invaluable assistance to the cardiologist for the determination of the presence and characteristics of certain abnormalities even in view of the limited nature of the device as described above.

As an extension of the prior art ECG scanning device described above, an improvement as shown in U.S. Pat. No. 3,718,772, issued Feb. 27, 1973, in the name of Clifford Sanctuary, provides for the reproduction of ECG signals from a single track magnetic tape recorder. Specifically, that reproducing system provides for recording at a very slow speed on a single track and then playing back at a high speed with provisions for the superimposition of the ECG complexes on a visual indicator such as an oscilloscope. Trigger signals to control the horizontal sweep are developed by the reproduction from the single track using a first playback trigger head. The trigger signals are delayed a particular period to provide for delayed trigger signals which control the sweep of the oscilloscope. This produces a stable superimposition of the ECG signals since the ECG signals are reproduced by a second playback head spaced from the first playback head. In this system, data is obtained from only one pair of ECG leads attached to the patient.

A further extension of the prior art is shown in U.S. Pat. application Ser. No. 430,704 now U.S. Pat. No. 4,006,737, issued Feb. 8, 1977 to Cherry and assigned to the assignee of the present invention, for an improved ECG scanning device for processing and observing large quantities of ECG signals in a relatively short interval of time, and in particular for providing an analysis of these large quantities of ECG signals. The scanning device of Ser. No. 430,704 provided for the processing and simultaneous presentation of ECG data from at least two pairs of leads located in different positions on the patient. Since more than one pair of ECG leads attached to the patient provided the cardiologist with different views of the same cardiac activity, the simultaneous presentation of the ECG information from at least two pairs of leads provided the cardiologist sufficient information to recognize an abnormality not obvious when viewing information obtained from a single pair of leads.

In order to increase the flexibility in the analysis of data with the ECG scanning device of the device of Ser. No. 430,704, the scanner was capable of playback not only in real time, but also at multiple high speed playback speeds. For example, the prior art device provided for playback speeds of 30, 60 and 120 times real time. The highest of these playback speeds was twice that previously obtained so as to provide for an obvious savings of time during the analysis of the superimposed information. The lowest of these high speeds was one-half the speed of that previously used to provide a slower presentation of the superimposed ECG complexes to allow better visual analysis of the recorded ECG information at critical time. Also, this slower playback speed allowed for the ECG signal to be connected to an external digital computer and with the information occurring at a slow enough rate so that the computer digitized the information with high resolution.

In order to achieve multiple high speed playback speeds and still provide realistic waveforms from the processed ECG information, the device of Ser. No. 430,704 included improvements in the tape deck and the circuitry associated with the tape deck to provide for proper performance. For example, the playback amplifiers had specific amplitude and frequency responses which were logically switched upon the selection of a particular playback speed so as to provide for accuracy in the reproduced ECG information. A variable tape-deck delay loop was used in combination with two spaced playback heads so as to provide a variable reaction time for manually switching from viewing superimposed ECG complexes at a selected high speed to a real time reproduction on a paper writer of the previously viewed ECG complexes. This was accomplished without the necessity of backing up the tape on the tape playback deck.

The device of Ser. No. 430,704 included a digital clock which was not only used to provide a visual indication of the time of day, but was also used to provide digital outputs of the time of day to the paper writer or any other external device. The digital clock might also be used to provide time synchronization of the processed data for use by external devices such as computers, paper writers, etc.

The device of Ser. No. 430,704 also included a heartbeat totalizer for providing a digital display of the number of heartbeats recorded on the magnetic tape. This heartbeat totalizer could provide either a display of the total number of heartbeats recorded on a complete tape, or could provide a display of the hour-by-hour total of the heartbeats. This digital display of either the total number of heartbeats or an hour-by-hour number of heartbeats was provided with the magnetic tape played back in either real time or at 30, 60 or 120 times real time or when the tape is moved in Fast Forward or Fast Reverse. In order to insure that the heartbeat totalizer is accurate, the device of Ser. No. 430,704 provided means to subtract heartbeats from the total when the tapedeck was in Fast Reverse. This allowed the identification and location of specific ECG complexes by number. The heartbeat totalizer also produced output signals of total beats or hour-by-hour beat totals for an external display such as a paper writer.

The device of Ser. No. 430,704 also provided an arrhythmia computer to detect and digitally display the numbers of premature ventricular contractions (VE) and supraventricular ectopic beats (SVE). The arrhythmia computer detected the VEs and SVEs from the magnetic tape at playback speeds of 30, 60 and 120 times the recorded speed. The arrhythmia computer provided either a display of the complete total or a display of the hour-by-hour total of the arrhythmia occurrences described above. In addition, the arrhythmia computer was designed to actuate event markers on a paper writer when the arrhythmia occurrences exceeded preselected number of occurrences during a predetermined time interval. In addition, the arrhythmia computer provided for a digital printout of the hour-by-hour totals of the arrhythmia occurrences.

The various printouts on the paper writer described above, plus novel trend data, which was analyzed from the recorded magnetic tape, was used with a multispeed multichannel, paper writer for reproducing analog data, digital printed data and event marking. This multichannel paper writer had the capability of writing two tracks of ECG data from the magnetic tape which had been recorded in real time and with the writing occurring at either of two writing speeds. The two tracks of ECG data from the magnetic tape were used at high speed playback to provide two channels of trend data. These two channels of information could be the heart rate and the ST segment level so as to provide for a scanning of an entire 24 hour tape in a period as short as 12 minutes. The paper writeout of the two channels of data, representing the heart rate and the ST segment level for the entire 24 hour period was provided on a relatively short piece of paper and was provided in the short time period such as 12 minutes. The paper writer also included the displaying of digitally printed data such as the time of day, arrhythmia and heartbeat totalization from signals generated in the ECG computer. The paper writer also provided for the automatic control of the paper speeds during the trend analysis so as to provide constant paper speed versus recorded time, even with different playback speeds. In addition, the paper writer could be rapidly switched from the high speed trend analysis to low speed ECG writeout with automatic control of the various parameters and responses.

The present invention is an extension of and, an improvement of the Electrocariographic Computer Device disclosed in Ser. No. 430,704. Specifically, the present invention includes recording two tracks of information on a miniature recorder which includes a built-in clock with a visual display. The recorder also includes an event marker, which may be activated when the patient experiences a predetermined event. For example, when the patient experiences some unusual heart activity or undergoes a predetermined physical activity or any other unusual occurrence, the patient pushes a button on the miniature recorder which momentarily interrupts the recording of information in one of the two tracks to record in place of the information a pulse burst as an event marker. At the same time, the patient may look at the visual time display and record on a log sheet the time and the nature of the event.

During playback, the present invention provides for a much greater degree of automatic processing of the tape so that the monitoring of the tape may be accomplished without the necessity of a technician visually observing the oscilloscope or monitoring an audible representation of the ECG signals. For example, during playback the computer may be set to provide a trend run so as to print out the trend analysis for the beginning to the end of the tape and then have the tape stopped automatically. Thereafter, the computer can be set to automatically cycle to the beginning of the tape to again print out the trend analysis, but with an automatic detection of various events. The detection of the various events are used to trigger the computer so that the tape is slowed down to real time to print out the portion of the ECG signals during the event. In other words, the technician does not have to monitor the playback to manually slow the tape down to real time as was done previously, but the computer itself senses the occurrence of an event during trend and slows the tape down to print out in real time the ECG signals and then speeds back up to the originally selected trend speed.

The present invention provides for the slow down to real time write-out during the trend analysis with the occurrence of events such as the occurrence of the event marker on the tape which has been placed there by the action of the patient. In addition, the computer may automatically detect the occurrence of an unusual event within the ECG signals to control the real time write-out. For example, the event may be various ectopic beats such as VEs or SVEs, an unusual level for the ST level, a rapid heart beat or a slow heart rate and any other unusual event which it may be desired to program into the computer.

In order to facilitate the control of the desired events which may be used to slow down the computer to real time, the arrhythmia computer may have a greater flexibility than the prior art arrhythmia computers. Specifically, the arrhythmia computer of the present invention allows for the selection of one or a number of parameters so that the operator has complete control as to what is to be the parameters of arrhythmia detection. For example, the operator can select such parameters as paired beats, degree of prematurity, width and amplitude. Any one of any combination of these parameters, may be controlled by the operator to provide for the event which will trigger the computer to slow down and print out the ECG signals in real time.

A clearer understanding of the present invention will be had with reference to the following description and drawings wherein.

FIG. 2, includes FIGS. 2, 2' and 2'' which when positioned side-by-side constitute a block diagram of the tapedeck control logic circuit for providing control of the tape deck at various speeds and in various directions in accordance with keyboard actuations.

FIG. 2(a) illustrates, in more detail, the brake logic circuit shown in FIG. 2.

FIG. 3 illustrates a schematic of the relay and motor interconnections to provide control of the motor at various speeds.

Figure 4:
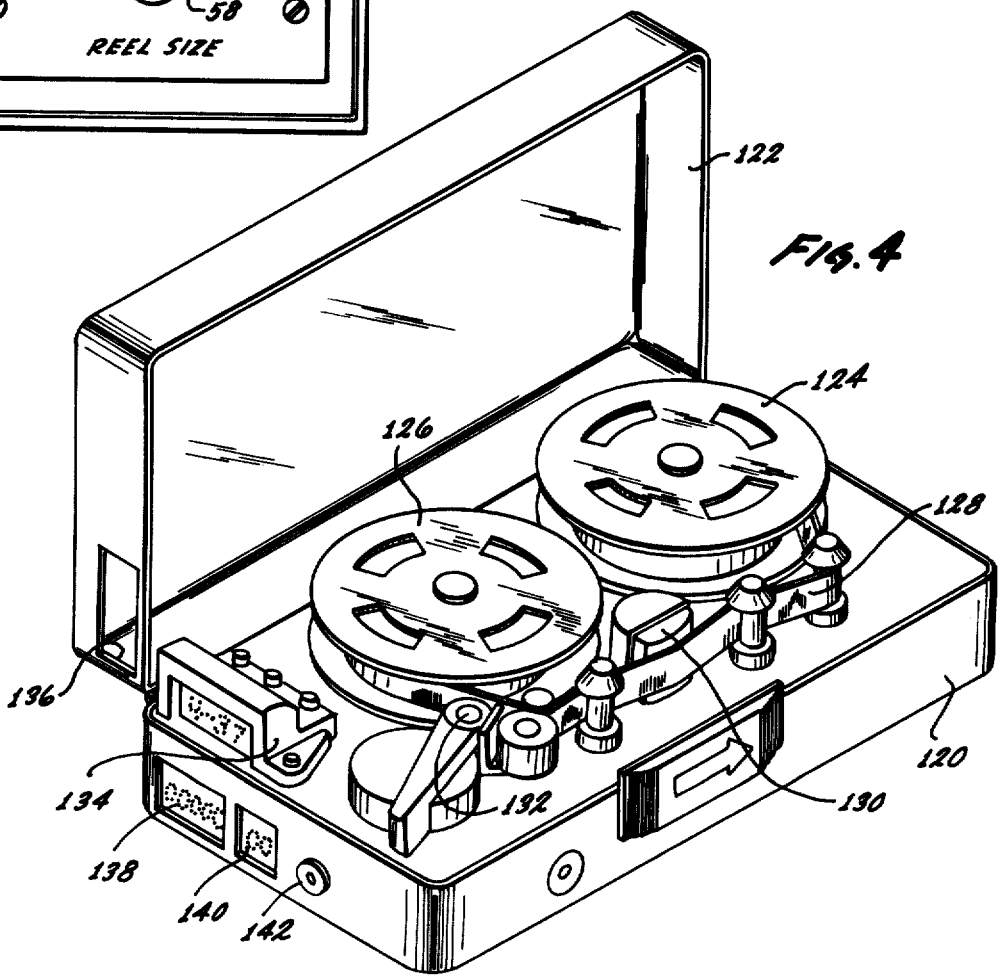

FIG. 4 illustrates the recorder to record ECG signals and including an event marker.

Figure 5:
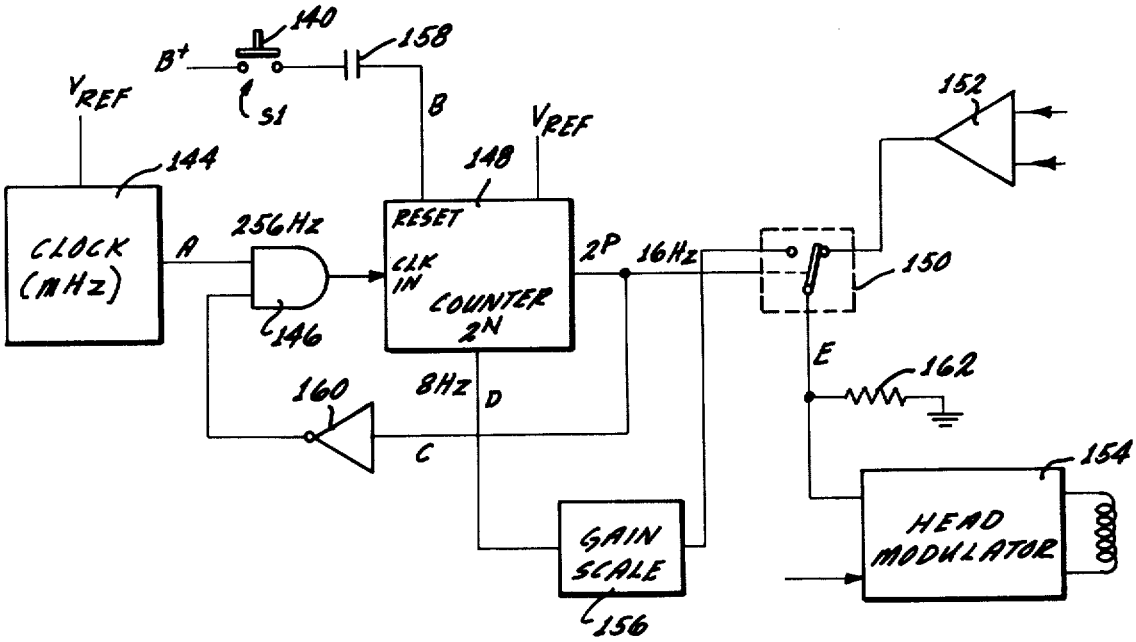

FIG. 5 illustrates a block diagram of the event mark pulse generator included in the recorder.

Figure 5A:
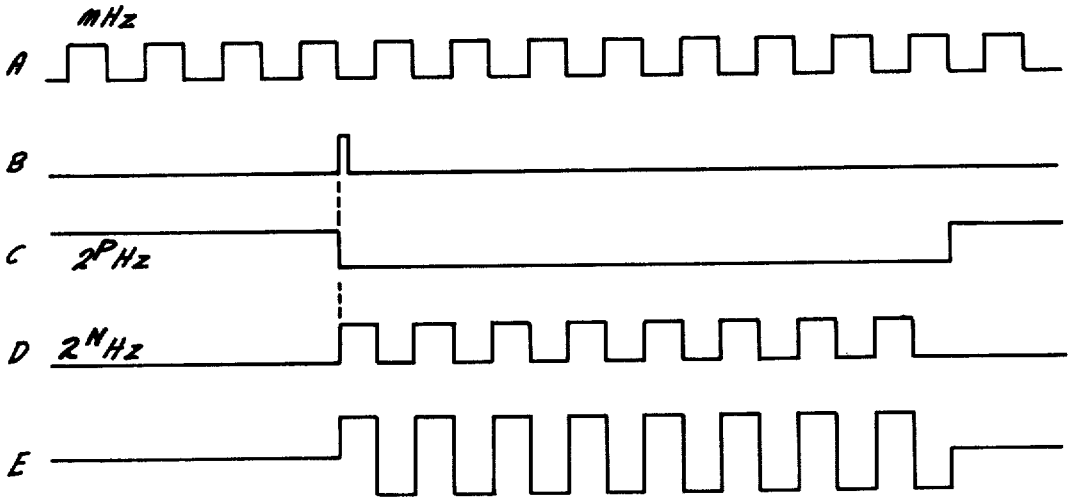

FIG. 5(a) are waveforms used in explaining the operation of the event mark pulse generator of FIG. 5.

FIG. 6 illustrates a schematic of the compensated head amplifiers for playback in real time and at multiple high speed playbacks.

Figure 7:
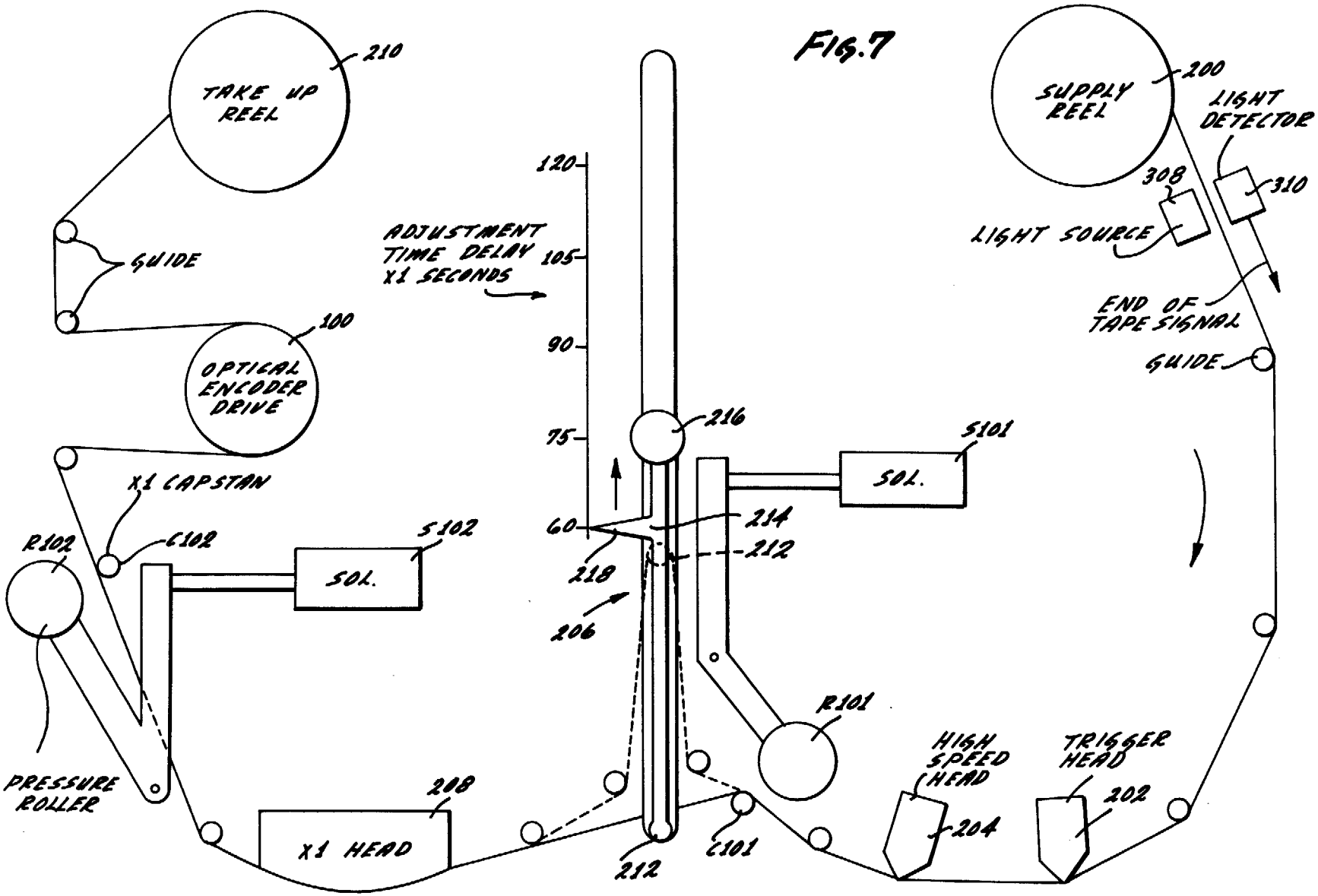

FIG. 7 illustrates the tape loop path from the supply reel to the tape reel and including a variable delay loop.

Figure 8:
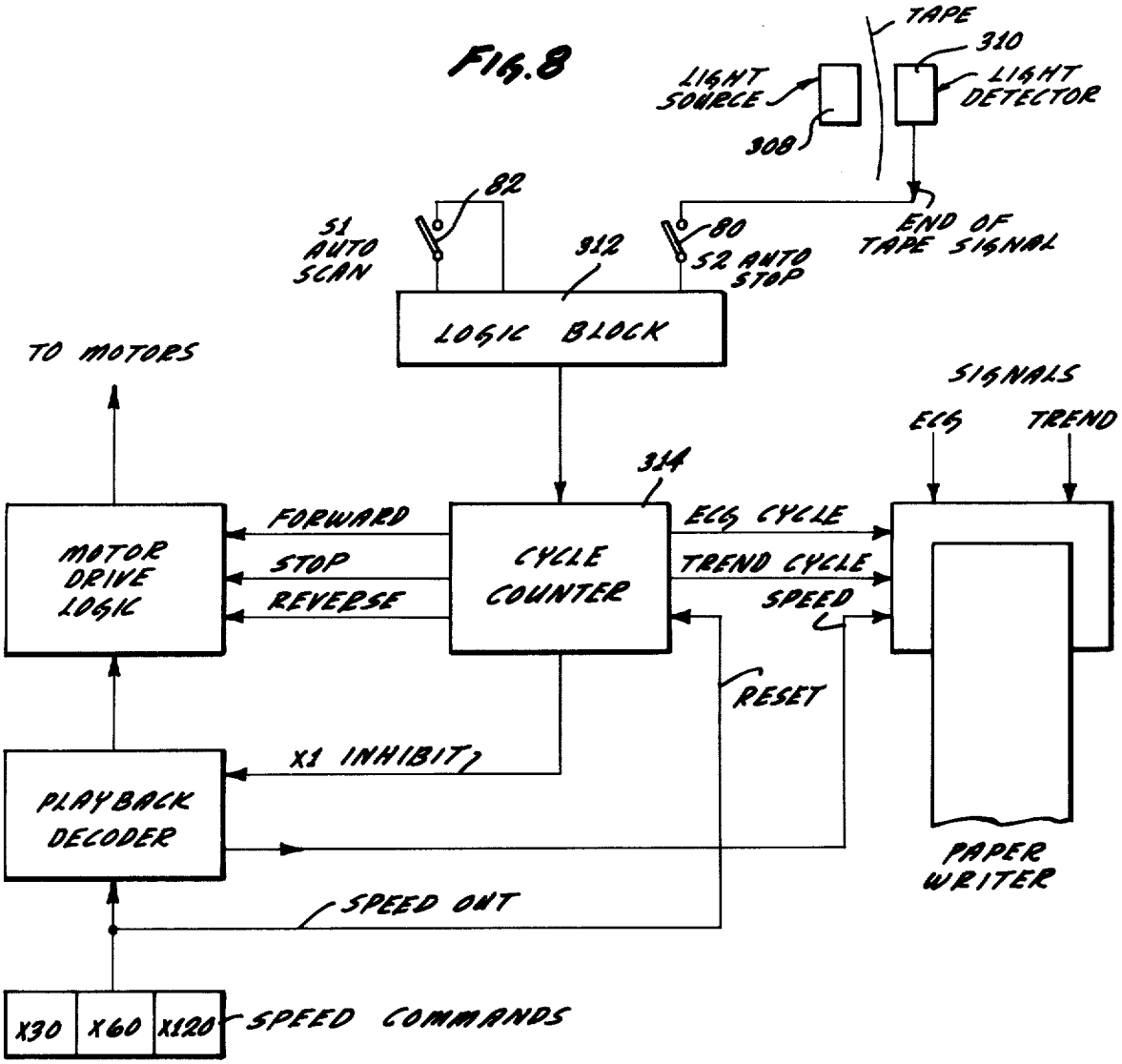

FIG. 8 illustrates a block diagram of the autoscan, autostop system.

Figure 8A:
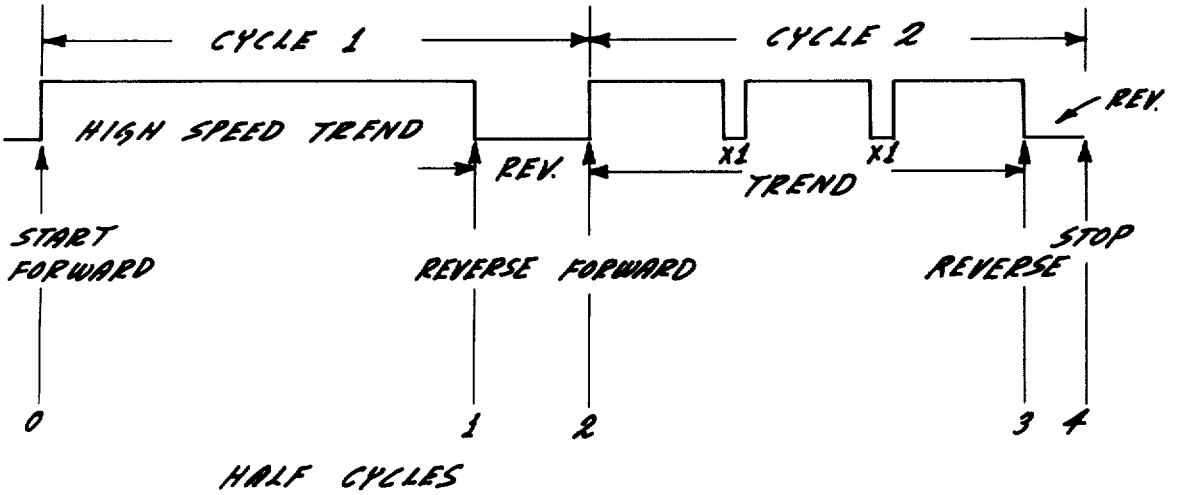

FIG. 8(a) illustrates the cycling of the tape during autoscan or autostop.

FIG. 9 illustrates a block diagram of a playback decoder for decoding the event mark from the high speed ECG signals.

FIG. 9a illustrates a typical write out of real time information during auto-scan.

Figure 10:
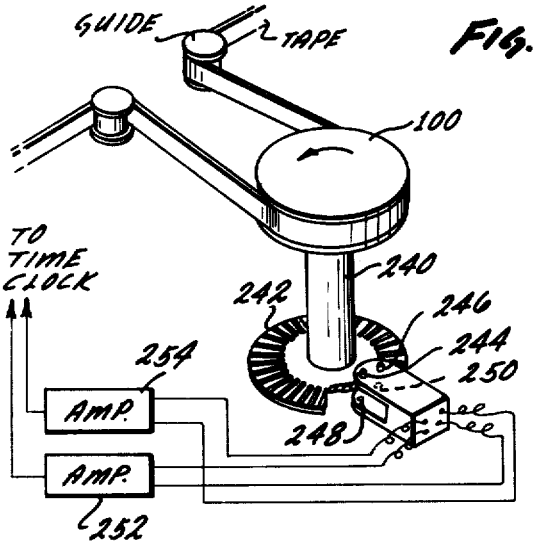
Figure 10A:
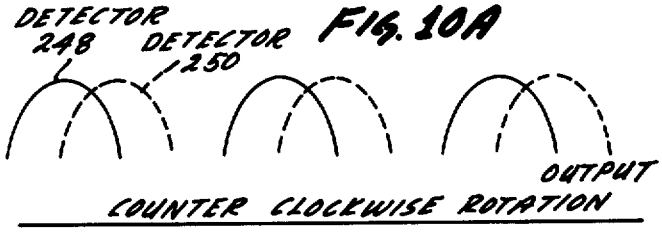

FIG. 10 illustrates the optical encoder for use in providing a clock signal in accordance with tape movement, and FIG. 10(a) are waveforms used in explaining the operation of the optical encoder of FIG. 10.

Figure 11:
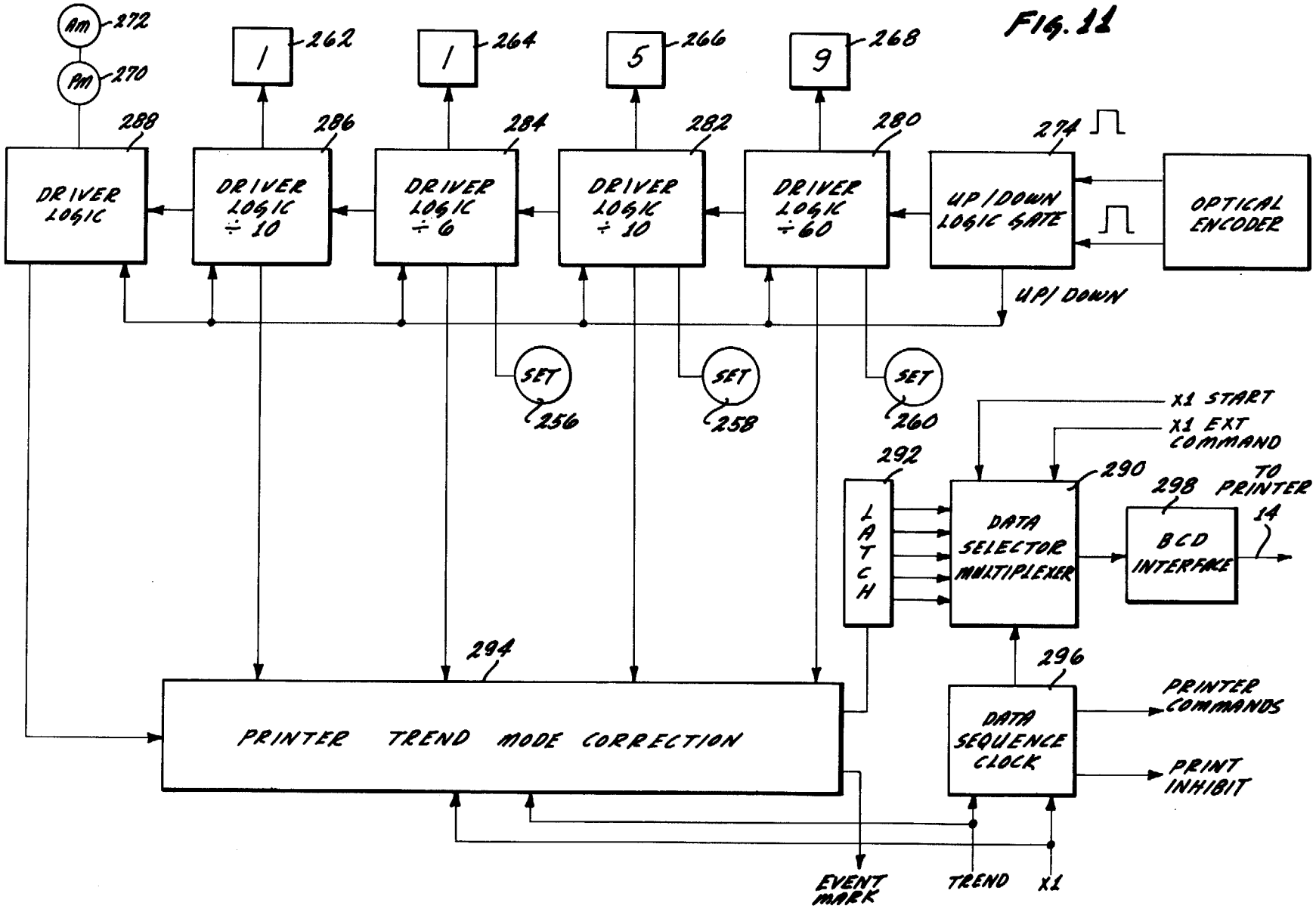

FIG. 11 is a block diagram of the digital clock and including the clock display.

Figure 12:
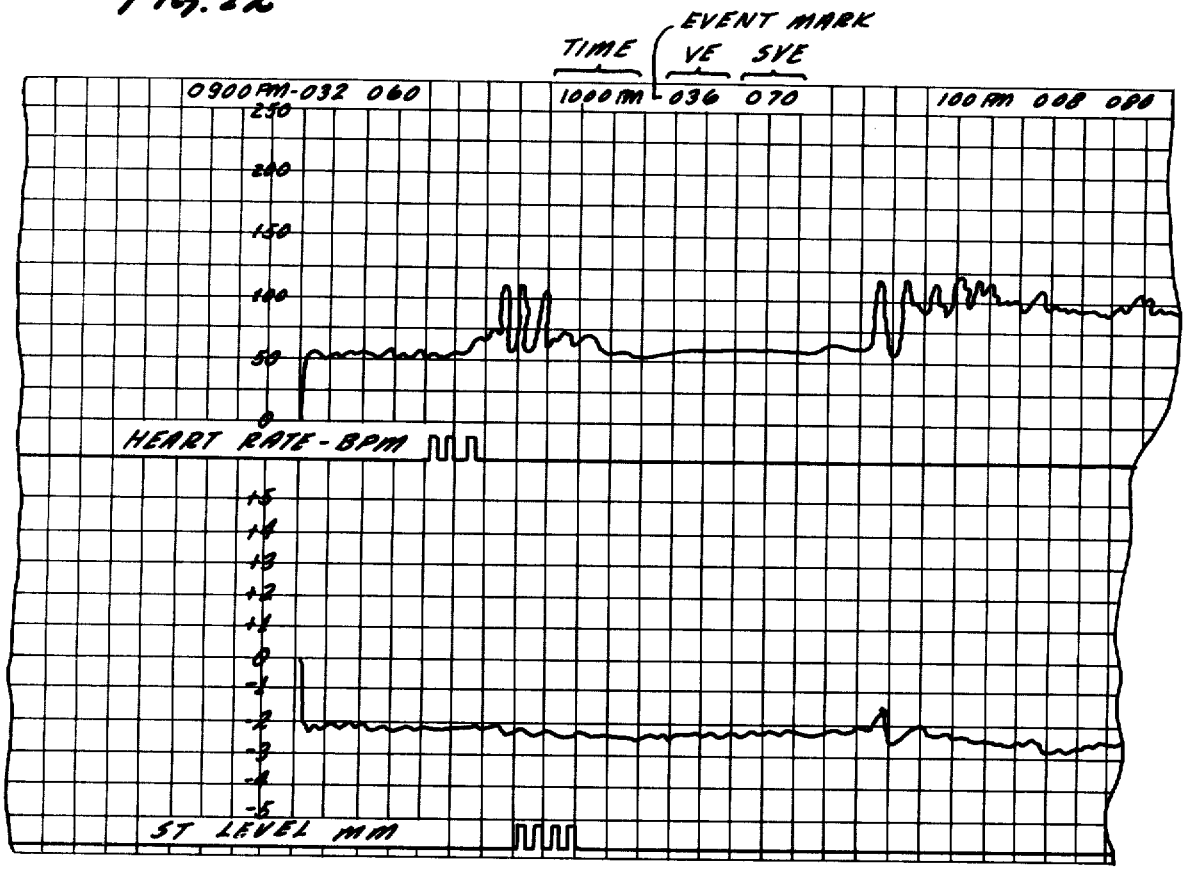

FIG. 12 illustrates a typical trend chart writeout including event markers and digital information.

Figure 13:
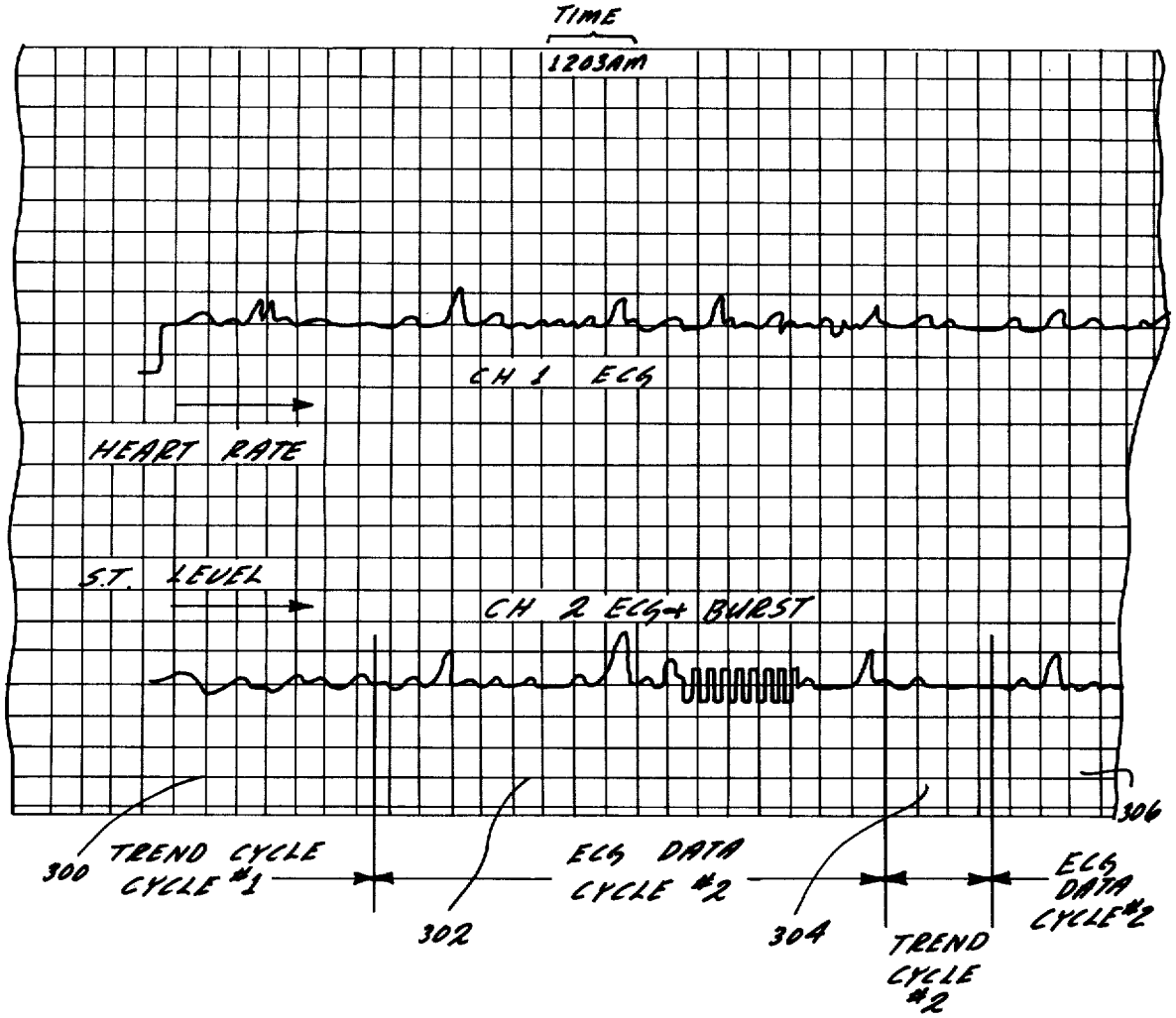

FIG. 13 illustrates a typical auto-scan chart writeout including trend information and real time information.

Figure 14:
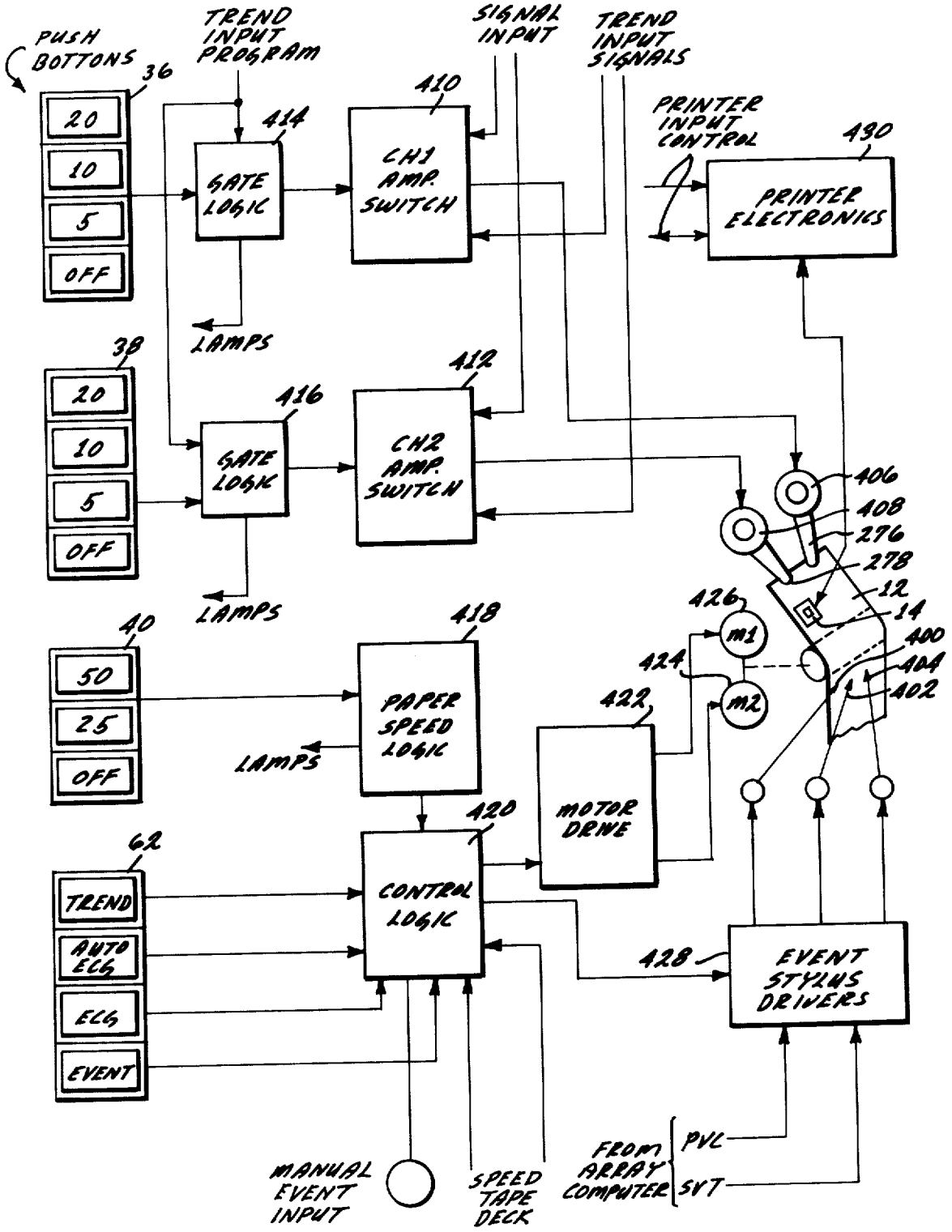

FIG. 14 illustrates a block diagram of the paper writer control system.

Figure 15:
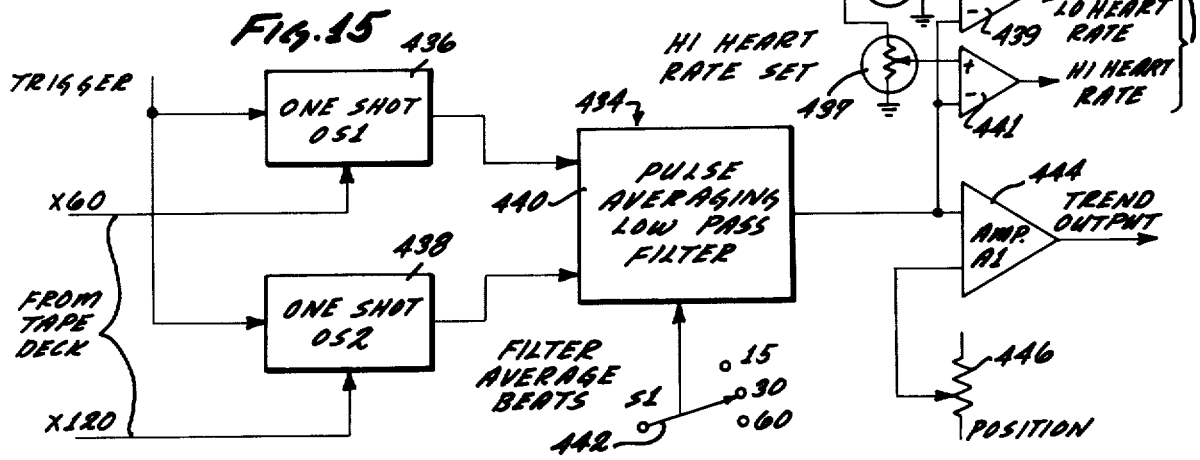
Figure 16:
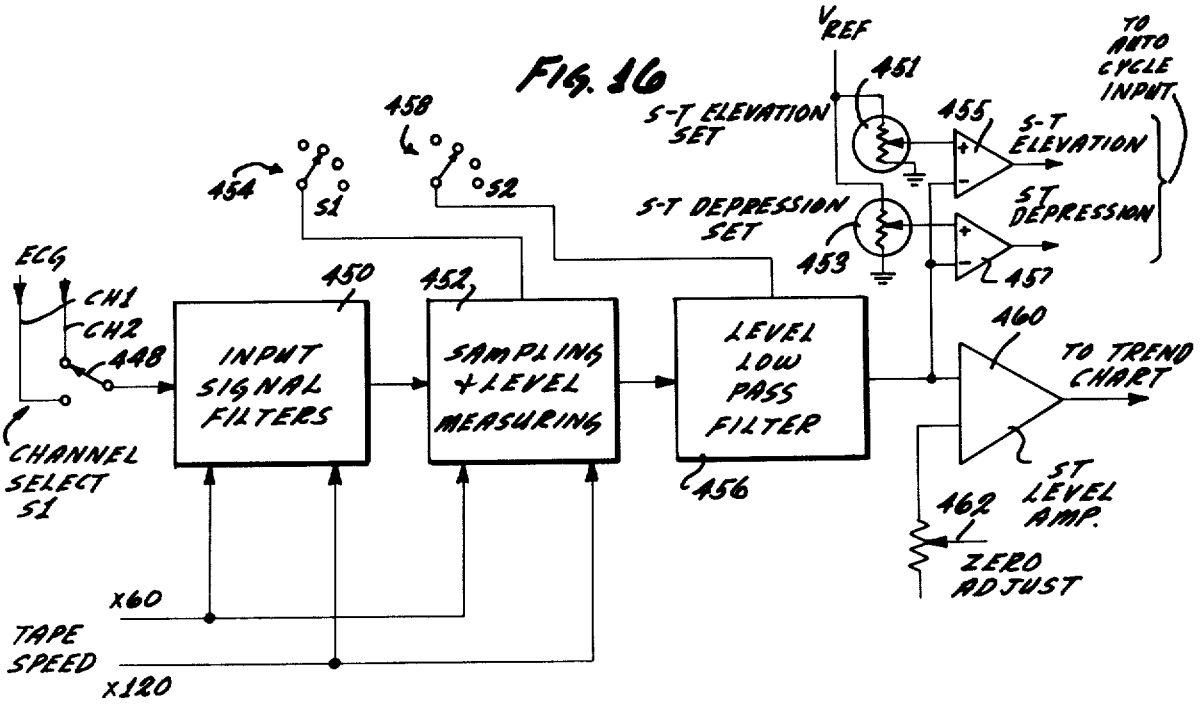
Figure 17:
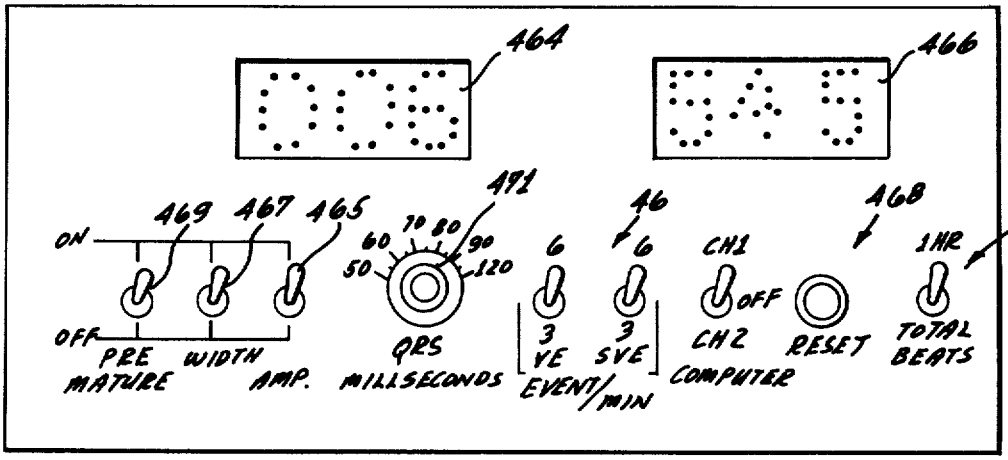

FIG. 15 illustrates a block diagram of a heart rate trend system to produce a trend output for the paper writer and event signals for the auto-scan FIG. 16 is a block diagram of an ST level system to produce a trend output for the paper writer, and event signals for the auto-scan FIG. 17 illustrates the front panel of the arrhythmia analyzer.

Figure 18:
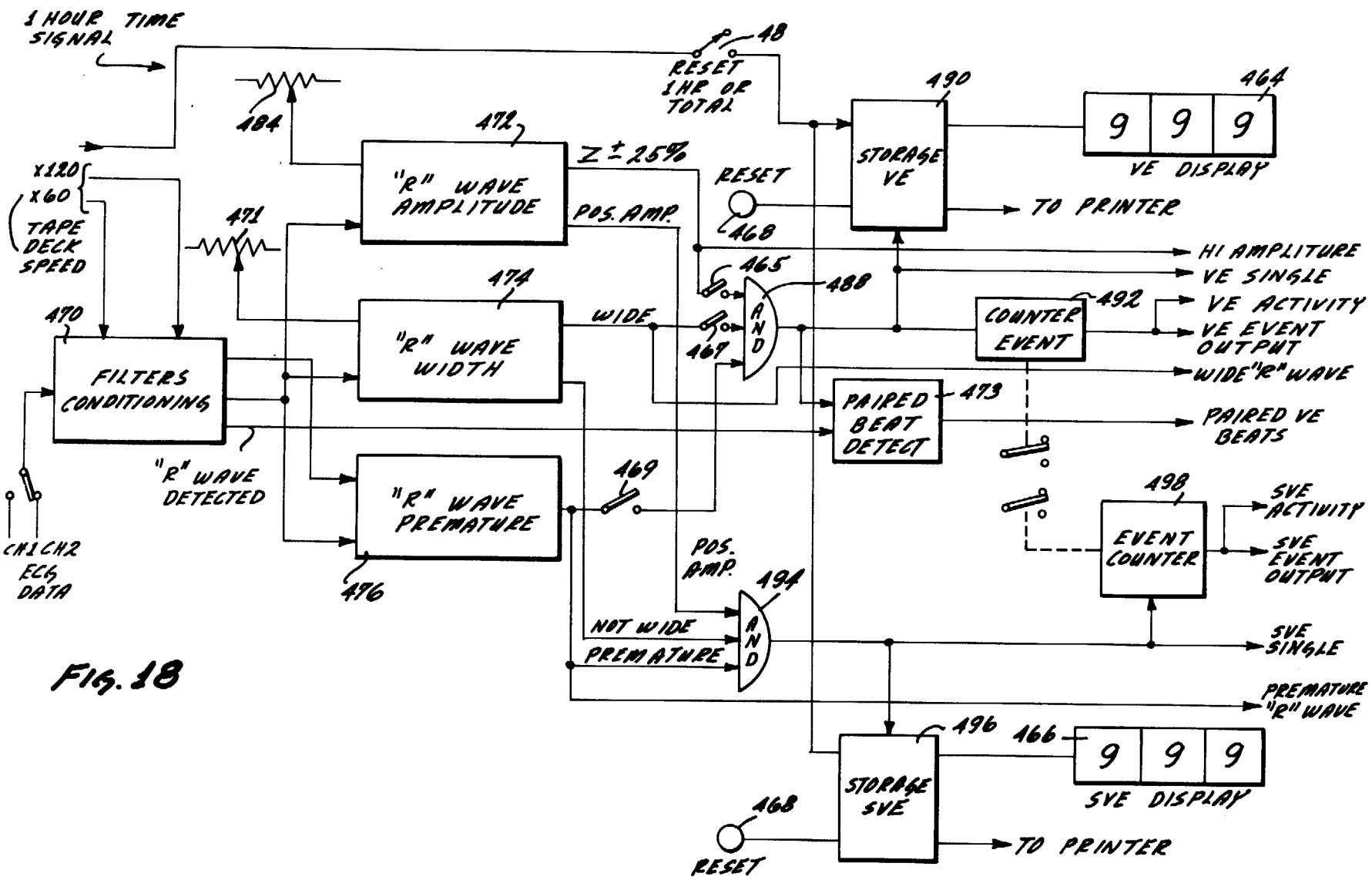

FIG. 18 illustrates a block diagram of the arrhythmia analyzer for supplying signals to the front panel shown in FIG. 17 and to the paper writer, and to the computer auto write.

Figure 18A:
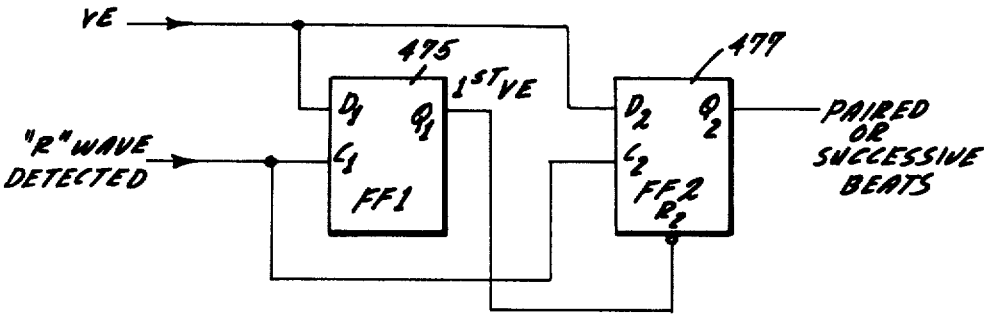

FIG. 18(a) illustrates a block diagram of the paired beat detector of FIG. 18.

Figure 18B:
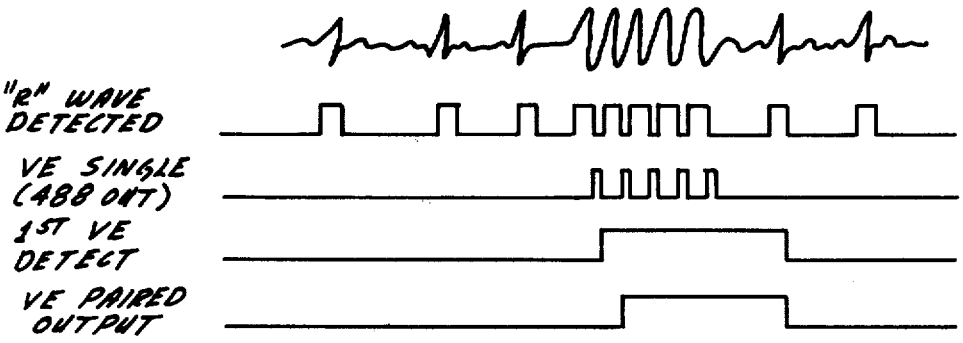

FIG. 18(b) are waveforms used in explaining the operation of the paired beat detector of FIG. 18(a).

Figure 19:
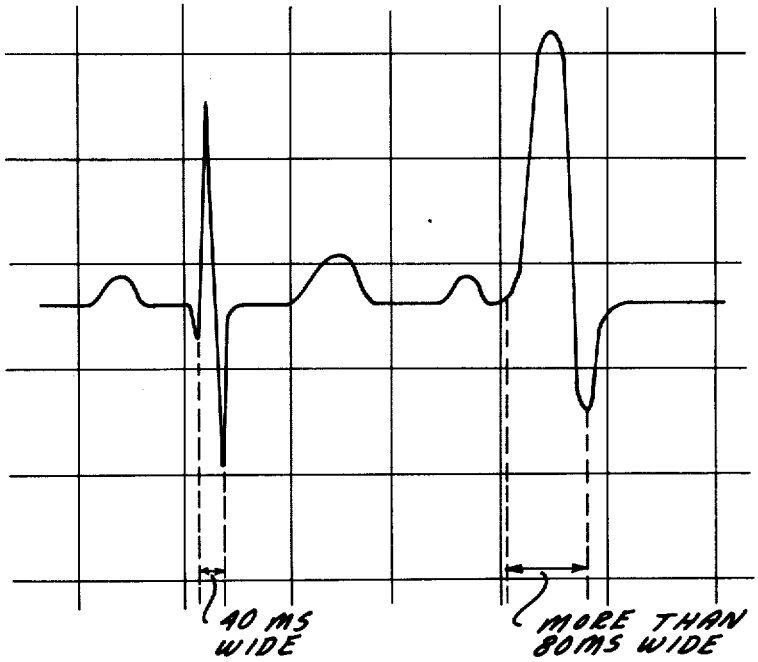

FIG. 19 illustrates a typical ECG complex as compared with an ECG complex with a wide QRS segment.

Figure 20:
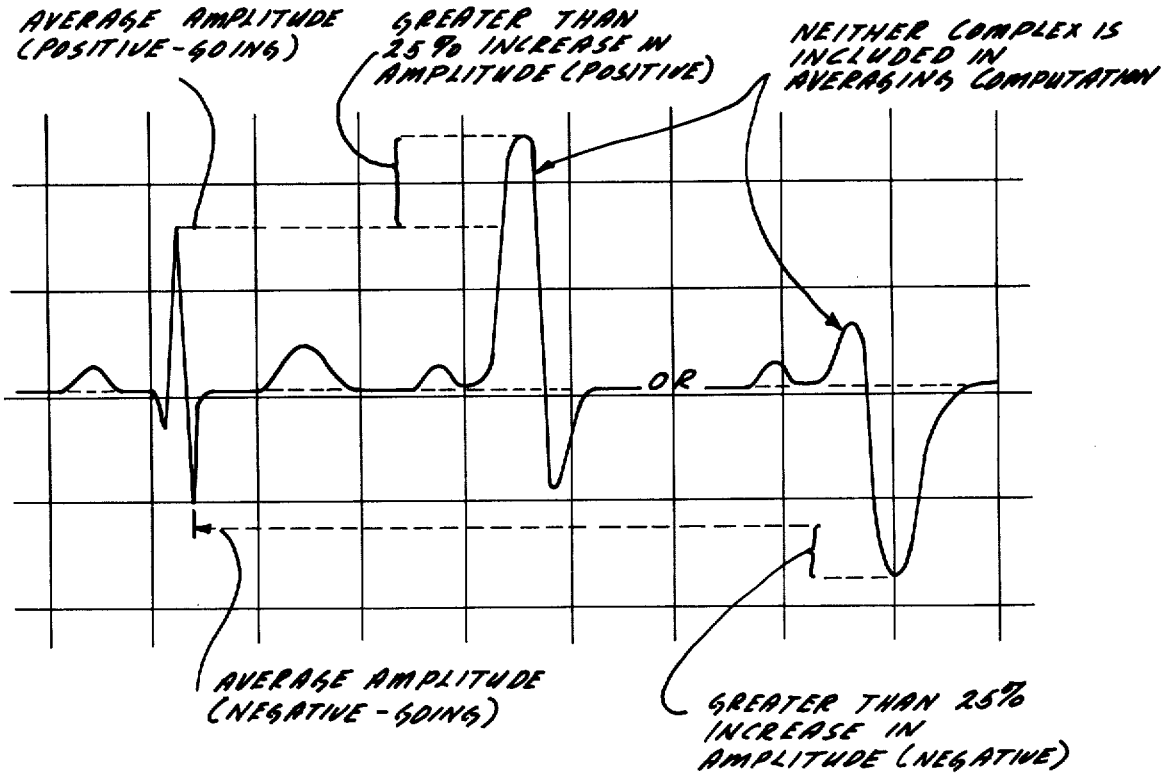

FIG. 20 illustrates a typical ECG complex as compared with ECG complexes having abnormalities in the amplitude of the QRS segment.

Figure 21:
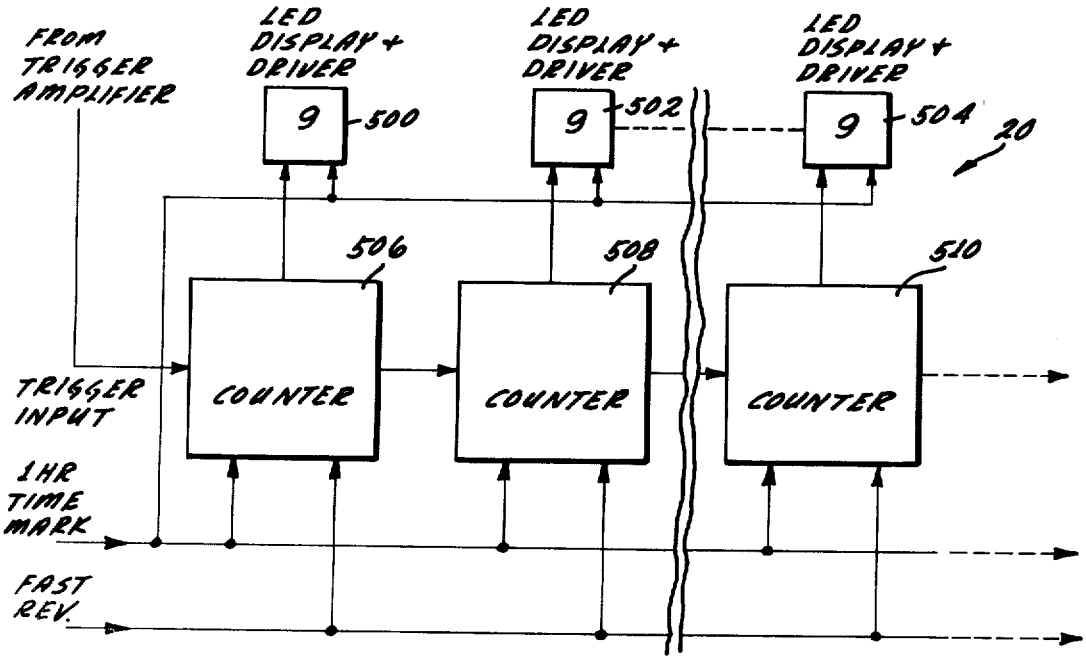

FIG. 21 illustrates a block diagram of a heartbeat totalizer including a heartbeat totalizer display.

Figure 1:
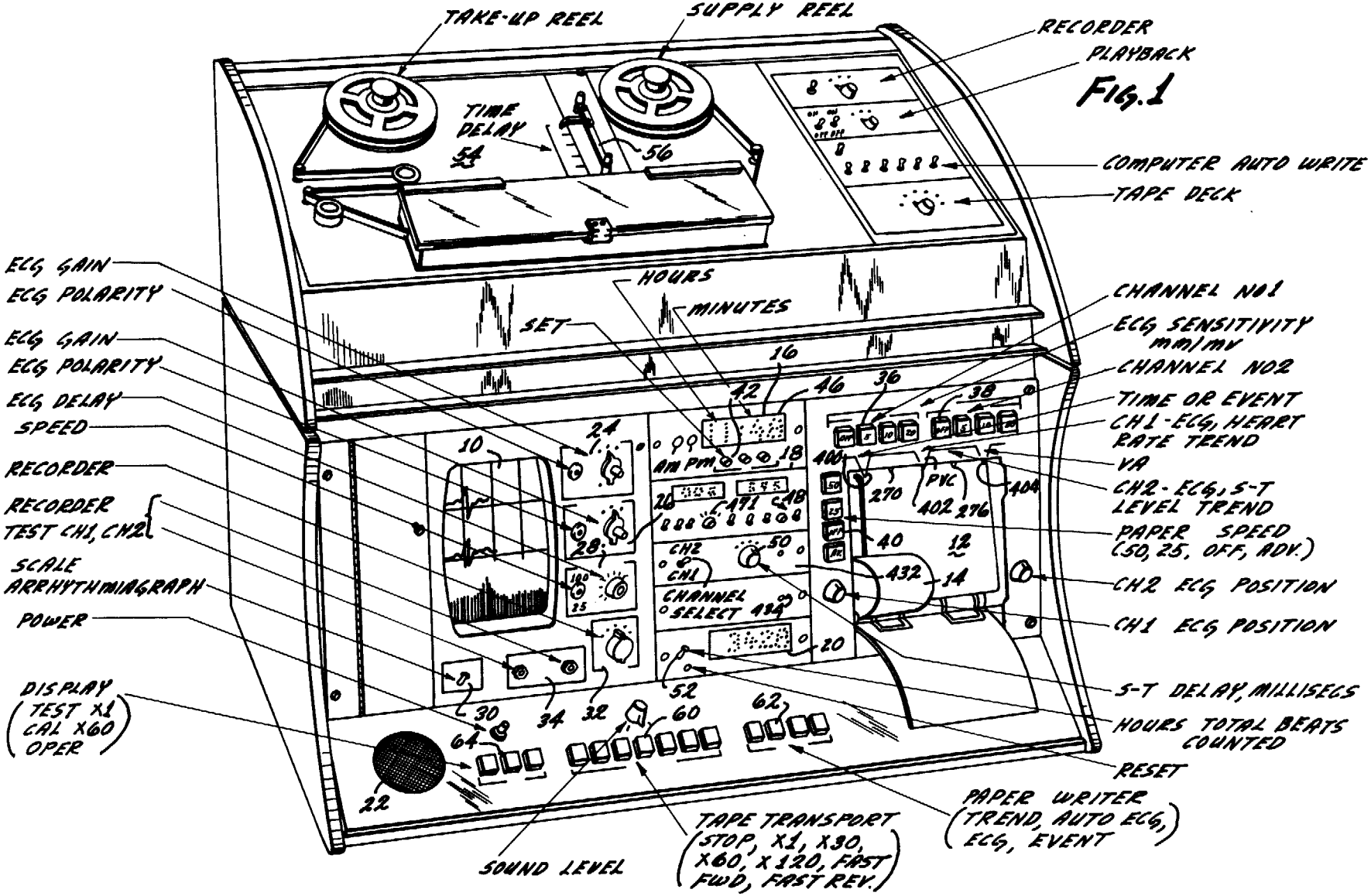
FIG. 1 illustrates an isometric view of an improved dynamic electrocardiography computer of the present invention, showing the front panel and the tapedeck and including a plurality of digital output indicators, an oscilloscope display, a paper writer, and an automatic computer control panel.

The present invention is an improvement of the electrocardiocomputer disclosed in application Ser. No. 430,704 and the disclosure of Ser. No. 430,704 is incorporated herein by reference.

in FIG. 1, an improved electrocardiocomputer of the present invention is shown. This computer provides for two channel playback of superimposed high speed ECG complexes and an arrhythmia bar graph all in the same oscilloscope display section 10. A two channel paper writer 12 includes in addition to the two channels of information, a plurality of event markers and a digital writer 14, to print digital information. In addition to the oscilloscope and paper writer, various digital displays are provided on the front panel, which include a digital time clock 16, an arrhythmia analyzer 18, and a heartbeat counter 20. An audio output may be provided by a speaker 22.

The various displays are controlled by control knobs and switches located adjacent to the display. For example, control sections 24 and 26 control the gain and polarity of the two channels of ECG information. Control section 28 controls the trigger delay for the sweep of the superimposed ECG complexes and also controls the speed of the sweep to widen the trace. The scale of the arrhythmia bar display is controlled by control section 30. A control section 32 varies the input amplitude of the signal from the recorder. The input from the two channels of the recorder may be connected directly into the input jacks in section 34 in order to provide for a recorder test.

The paper writer 12 may also include controls such as controls 36 and 38 to vary the sensitivity of the paper writer in the two channels. The paper speed may be controlled by a group of push buttons 40.

The digital time clock includes setting buttons 42 to set the time and setting buttons 44 to set either AM or PM. The arrhythmia analyzer includes switches 46 to control a predetermined number of events per minute to be exceeded, and a swtich 48 to control the totalizing either in an hour period or cumulatively. The ST level trend computer includes an ST delay control 50. The heartbeat computer includes a switch 52 for either one hour totals or cumulative totals.

The tape transport section 54 includes a variable delay tape loop 56 and an adjustment switch for different reel sizes 58. In addition, the master panel includes a plurality of push buttons 60 to control the tape speed and direction. A plurality of push buttons 62 control the paper writer to provide different output writing modes. A series of push buttons 64 provide a control of the oscilloscope display. The reel size switch is included in an automatic computer control panel 66 divided into a recorder section 68, a playback section 70, a computer auto write section 72 and a tapedeck section 74.

Figure 1A:
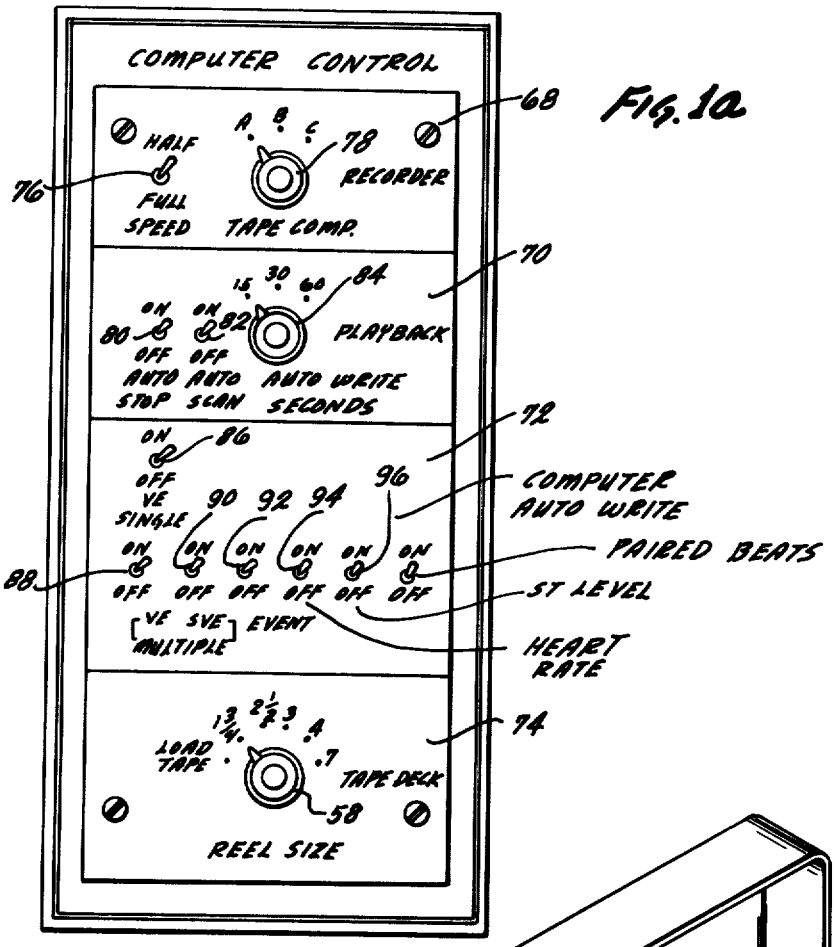
FIG. 1(a) illustrates a detail of the panel of FIG. 1 and specifically shows the automatic computer control panel.

FIG. 1(a) illustrates in greater detail the automatic computer control panel 66 including recorder section 68 playback section 70, computer auto write 72, and tape deck section 74. Tape deck section 74 includes the reel size switch 58 which is used to provide for adjustments in accordance with the reel size of the tape used with the ECG computer of the present invention.

The recorder section 68 includes a switch 76 which is positioned in accordance with the speed in which the recorder recorded the ECG signals. For example, the prior art recorders recorded the information at a speed such as ⅛ inch per second. In order to maximize the recording time and minimize the size of the recorder, the present inventiom may operate with a recorder that records information at half that speed, such as 1/16 inch per second. In order to compensate for this lower recording speed and allow the ECG computer to service all prior art recorders the switch 76 may be positioned either at a full speed position or a half speed position. In the half speed position of switch 76 the real time playback is at twice the speed as before, so that the size of the real time playback head need not be increased. The ECG computer must have the other controls designed so that the playback, although at twice the speed, appears to be at real time or at a preselected multiple of real time. For example, the paper recorder can be run at twice the speed as before and the other portions of the computer operated so as to compensate for the increase in the playback speed of the recording tape. The recorder section 68 also includes a tape compensation switch 78 which has three positions which are set in accordance with needed compensation of the recording tape in accordance with the original recording speed and other factors.

Play back section 70 includes an autostop on-off switch 80, an auto-scan on-off switch 82 and an auto-write rotary switch 84. The autostop switch 80 controls the playback during trend to automatically stop the tape at the end of a trend run. The auto-scan switch 82 controls the computer to cycle the trend analysis back to the beginning of the tape and then allows an automatic scan of the tape at high speeds with periodic reduction to real time write out in accordance with particular events. The auto-write rotary switch 84 provides an adjustment for the amount of real time write out each time the tape is automatically reduced to real time in accordance with the detection on an event.

The computer auto-write section 72 includes a switch 86 which controls the tape during auto-scan to write out in real time upon the occurrence of a single VE event. Switches 88 and 90 provide for automatic write outs in real time upon the occurrence of multiple Ve or SVE events, in accordance with preselected parameters, set by the arrhythmia analyzer 18. An on-off switch 92 controls the auto-scan write out real time in accordance with detection of an event burst which has been placed on the tape by the patient upon the activation of the event button. In addition to the switches 86, 88, 90 and 92, any number of additional event switches may be incorporated such as switches 94 and 96 to control the auto-scan to write out real time ECG signals, in accordance with events such as a heart rate event or an ST level event. In addition, other specific events which may be included to control auto-scan write out will be gone into in greater detail at later portions of the specification.

It is to be appreciated that the above description of the overall outward appearance of the ECG computer of the present invention is general in nature and in many instances, more specific details will be included at a later portion of this specification. For example, not every control element has been described and some elements which have been described are self-evident and conventional in their operation and may not be described in much greater detail.

Generally, the improved ECG computer of the present invention is a high speed ECG scanning device that documents abnormalities from a long term ECG recording such as a recording over a 24 hour period using two pairs of leads to provide two channels of ECG information. This ECG information may be displayed in superimposed form at 30, 60 or 120 times real time, or as normal ECG traces in real time on the display oscilloscope 10. This display oscilloscope 10 provides a single multiscan display to provide both ECG traces an an arrhythmia bar trace simultaneously on the same cathode-ray tube.

The digital time clock 16 accurately displays tape time and relates it to the time of recording when preset at the start of the tape. A two channel paper writer 12 provides documentation of the ECG data being reviewed in the ECG real time mode. The time of day of each selected paper writeout is automatically printed on the electrocardiograph paper.

In addition to the writeout of the ECG data, the ECG computer includes specific analysis sections 434 and 432 to obtain heart rate and St segment data and event data from either of the ECG lead positions. This data is fed to the paper writer 12 when the tape is programmed to be in the high speed mode to provide a trend chart of heart rate and ST segment in as little as 12 minutes from a 24 hour recording and to provide an auto-scan showing trend and real time data in accordance with event detection.

The heartbeat counter 20 provides the total number of heartbeats which occur either on an hour-by-hour basis or on a cumulative basis. The arrhythmia analyzer 18 provides digital displays of the numbers of ventricular and supraventricular ectopic beats that occur on either a per-hour basis, or on a cumulative basis and also provides event data. This data may also be recorded digitally on the paper writer by the digital writer 14 and the event data may be used to control the auto-scan between high speed and real time write out.

As shown in FIG. 1, a group of push button switches are shown at position 60 to control the operation of the tapedeck. FIG. 2 illustrates these same push buttons for use in controlling the tapedeck control logic system. The push button switches are momentary contact typewriter-type keys, which include built in indicators so as to provide a memory visual display of the present keyboard state. The push buttons are labeled, "Stop," "X1," "X30," "X60," "X120," "Fast Forward," and "Fast Reverse." The Stop key does not have an indicator lamp. The general operation of the control of the tapedeck in accordance with the particular key activated and with reference to FIG. 2, is as follows:

In the Stop mode, the tape does not move, but one of either motors M103 or M104 has torque to pull the tape. The other one of the motors M103 or M104 acts as a DC dynamic brake to hold the tape in a Stop position. The motor which acts as a DC dynamic brake is controlled to provide a force slightly larger than the takeup torque value. Either of the motors M103 or M104 may act as the brake, depending on the previous running state of the tape transport. For example, if the previous state was fast forward (FF) or playback at any speed, then after the stop button is operated, the torque remains on the fast forward motor M104. If the previous state was fast reverse (FR), then after the stop button is operated, the torque would remain on the fast reverse motor M103, and the brake would be provided by the fast forward motor M104. The above described system provides a tape-tensioning design to keep the tape tight around the tape loop at all times. It is especially important that the tape is tight around a clock pulley 100 which pulley is used to drive an optical encoder to produce a clock time signal.

In the X1, or real time mode, the X1 capstan roller R102 is controlled by the X1 capstan solenoid S102 to move towards the magnetic tape and engage the X1 motor capstan C102. In this mode, the fast forward motor M104 is operated at low torque and the fast reverse motor M103 acts as a dynamic brake.

In the X30, X60 and X120 high speed playback modes which are 30, 60 and 120 times real time, the high speed capstan roller R101 is activated by the high speed capstan solenoid S101 to move toward the magnetic tape and engage the high speed capstan C101. The fast forward motor M104 is operated at a higher torque than in the X1 mode. The fast reverse motor M103 acts as a dynamic brake, but at a lower value than in the X1 mode, since the supply reel of tape 200 is moving at a greatly increased speed. By activating the desired one of the X30, X60 or X120 keys, the speed of the high speed capstan motor is controlled to operate either at 900, 1,800, or 3,600 rpm.

In the Fast Forward and Fast Reverse mode, a large torque is applied to the applicable motor and with a small dynamic brake to the other one of the motors. This keeps the tape tight during starting and fast rewind, so that the tape does not slip around the digital clock pulley 100. If the direction of fast rewind is changed from fast forward to fast reverse, or from fast reverse to fast forward, the torque and dynamic brake are also reversed, so that the tape reverses direction without throwing a tape loop. The tape first stops slowly, then increases in speed since the motors are controlled to always have one reel pulling and one reel holding back independent of the direction of tape travel.

In order to change from one mode to another, the logic design of FIG. 2 is designed to provide rapid mode changing from any condition without a tape loop or loss of tension. This is important, since a loss of tension around the clock pulley 100 would cause time errors. To achieve this, the design has certain automatic features that prevent particular conditions from occurring. For example, during rapid fast forward tape travel, it is impossible to activate the X1, X30, X60 or X120 keyboard switches. Such an activation would cause a tape foul-up, since the tape would still be moving at a high speed and depending upon the reel size, and the amount of tape on the reel, the normal inertia may keep the reel moving several seconds. This would be true for either Fast Forward or Fast Reverse mode, so that the system of FIG. 2 includes memory circuits that make the tapedeck automatically go to a Stop mode if any other key such as X1, X30, X60 or X120 is activated after a Fast Forward or Fast Reverse mode.

As indicated above, the system is specifically designed to keep adequate tape tension around the digital clock pulley 100 under all possible modes of operation or changes from any mode to any other mode. This it to insure that the pulley 100 accurately moves in relation to tape movement to provide for a reliable indication of the time of day relative to the tape position once the initial starting time for the tape has been preset.

As shown in FIGS. 1 and 2, a rotary switch 58 is used to adjust the take-up torque for operation in either Fast Forward or Fast Reverse and also adjust the dynamic brake used in stopping the tape and in the playback of the tape for reel sizes of $1\frac{3}{4}$, 3, 4 and 7 inch.

Turning specifically to FIG. 2, the motor M101 is a three speed synchronous motor that runs at either 900, 1,800, or 3,600 rpms by connecting poles in the motor in different configuratins. This type of motor is commercially available and one such motor which is available bears model number NCH-13, B7122XZ, 115V, 50/60 HZS, 900/1800/3600, and is manufactured by the Bodine Electric Company of Chicago, Illinois. This motor uses a total of 7 input wires and by varying the connection to these input wires, gives the three desired speeds of 900, 1,800 and 3,600 rpms. The motor, M101, is connected through a pulley P101 and a drive belt B101 to drive the high speed capstan configurations. to as to provide tape speeds of $3\frac{3}{4}$, $7\frac{1}{2}$ and 15 inches per second. The X30, X60 and X120 push buttons change the logic circuit L1 to provide output signals to two relays K1 and K2, which in turn provide the proper connections to the motor M101 to produce the three seeds. Motor M101 is controlled to always run at one of its three speeds and may then be changed to any other speed.

Since the motor is always maintained at its last operational mode speed, a fast transfer may be made to any other speed since the motor is already moving and does not have to be started from a rest position. The speed modes may therefore be rapidly changed with minimum delay to provide very rapid analysis between a high speed superimposed scan and a low speed X1 writeout.

The motor M102 is used to drive the tape at X1 speed and uses a capstan C101. The X1, or real time speed of the tape is 7½ inches per minute which provides for the recorded tape containing information for a long period of time, such as 24 hours. As indicated above, the two motors M103 and M104 provide fast reverse and fast forward functions.

The fast playback motor M101 generally provides for the three different playback speeds of X30, X60 and X120, by the use of an 8 pole motor and by choosing either two, four or eight poles within the motor to provide the different speeds of rotation. The keyboard switches, X30, X60 and X120 provide momentary signals which activate the logic block L1 to set it in any one of three states. In addition, as shown in FIG. 2, reset inputs from any of the other keyboard contacts shown in FIG. 2 return the logic L1 to the initial state.

As indicated above, the drive motor M101 is commercially available and includes 7 input wires designated W1 through W7. The specific interconnection of the AC line voltage by the relays K1 and K2 to the wires W1 through W7 is shown in FIG. 3. The relays K1 and K2 are controlled by signals from the logic block L1. The relays K1 and K2 in combination provide multipole double throw contacts to insure rapid switching from one speed to another without the use of rotary selectors. Specifically, the desired output speed for the motor M101 is obtained by the interconnection of the windings W1 through W7 using four pole double throw contacts. The logic block L1 controls the relays K1 and K2 in the following relationship and where the speed "S" at the different high speed playback speeds is as follows:

$S\ X30 = K1 \cdot K2$ $S\ X60 = K1 \cdot K2$ $S\ X120 = K1 \cdot K2$

FIG. 3 specifically shows the interconnection of the 7 wires, W1 to W7, to the multipole contacts controlled by the relays K1 and K2. At the X120 speed, one side of the AC line is connected to windings W1 and W4, the other side of the AC line is connected directly to winding W6 and the other side of the AC line is connected through the starting capacitor C1 to winding W7. The capacitor C1 is used to apply starting torque to the motor M101. With this interconnection the motor operates as a two pole motor at 3,600 rpms. At the X60 speed, one side of the line is connected directly to the windings W1 and W2 and the other side of the line is connected directly to the winding W4 and through the starting capacitor C1 to the winding W5. With this interconnection the motor operates as a four pole motor at 1,800 rpms. At the X30 seed, one side of the AC line is directly connected to winding W1 and the other side of the AC line is connected directly to the winding W2 and through the capacitor C1 to winding W3. The motor now operates as an eight pole motor at 900 rpms.

The motors M103 and M104, shown in FIG. 2, are used to transport the magnetic tape in either direction during the Fast Forward or Fast Reverse commands. The motor M104 is also used to drive the tape take-up reel during the normal Play mode. During Fast Forward, or Fast Reverse, the two capstans C101 and C102 are not activated. A relay K3 is activated in the Fast Reverse mode to apply the line voltage to the motor M103. At this time, dynamic braking is applied to the motor M104 to keep the tape tight across the heads and around the clock pulley 100.

In the Fast Forward, or Play modes, at either the X1, X30, X60 or X120 speeds, AC line voltage is applied to the motor M104, using relays K4 and K5 and in accordance with the position of the reel size switch 58. As shown in FIG. 2, the reel size switch 58 varies the voltage input in predetermined increments in accordance with a group of resistors. The relays K4 and K5 are used to short out the resistors R1 and R2 so as to drop the AC voltage to different levels to provide different takeup torques. For example, a torque level "A" allows Fast Forward or Fast Reverse operation with relays K4 and K5 activated. A torque level "B" which is slightly lower is used during high speed playback at the X30, X60 and X120 speeds and is provided only when relay K5 is activated. A torque level "C" is used to provide a take-up torque for the X1 mode or the Stop mode and is provided when neither of the relays K4 and K5 is activated.

The control logic system for the tape transport is shown in FIG. 2 as a plurality of logic blocks L1 to L10. Each logic block is formed from a plurality of conventional logic gates and flip-flops. It is to be appreciated that the interconnection of these logic gates and flip-flops to form logic blocks L1 through L10 is of conventional design and will generally be described using logic equations. These equations are fully representative of the particular functions of these blocks and since the specific design of the logic blocks in and of themselves form no part of the invention, these equations and other descriptions are used to avoid excessive length in the description of the present invention.

The logic blocks L1, L2, L3, L4 and L5 are connected to the 7 push button switches shown in FIG. 2 and with each logic block including a flip-flop memory so as to hold the last state of operation. In addition, each of the 7 push buttons resets the other logic blocks so that any condition may be maintained.

As indicated above, the logic block L1 decodes the X30, X60 and X120 buttons to activate relays K1 and K2 to achieve the three motor speeds from the motor M101.

Logic blocks L3 and L6 work in combination with the keyboard inputs "Fast Forward" and "Fast Reverse" and "X1" and "Play" (where play = X30 + X60 + X120) to control relays K4 and K5. The operation of the relays K4 and K5 control the take-up torque "T" at three levels "A," "B," or "C," of either the fast forward or fast reverse motors. The three levels of torque described above follow the logic equations, $\text{Torque A} = FF + FR = K4 \cdot K5$ $\text{Torque B} = (\text{Play } X30 + X60 + X120) = K4 \cdot K5$ $\text{Torque C} = \text{Stop} + X1 = K4 \cdot K5$ The logic block L5 is a simple set-reset flip-flop which stops the tape motion by resetting all other logic groups, releasing the capstan pressure roller, setting up the condition for the low torque level torque "C" on either the fast forward or fast reverse motor and increasing the DC dynamic brake on the supply motor.

The logic groups L2 and L4 determine the status of the high speed capstan C101 and the low speed capstan C102 and provide outputs to the applicable capstan drives D1 and D2. These capstan drives D1 and D2 in turn drive the high speed capstan solenoid S101 to activate the high speed capstan roller R101, or to drive the X1 capstan solenoid S102 to activate the X1 capstan Roller R102. the logic equations provided by logic groups L2 and L4 in accordance with the activation of particular keyboard inputs are as follows:

Play = D1 + (X30 + X60 + X120) I

X1 = D2 · I where

I = Inhibit after FF and FR

An inhibit signal I from logic group L10 and flip-flop FF1 is also applied to logic groups L2 and L4 so as to prevent the capstan solenoids from being applied immediately after the tape is moving at high speed in either the Fast Forward or Fast Reverse mode. If either of the capstans were activated while the tape was traveling at high speed, tape breakage could occur. The inhibit signal I is formed from the memory flip-flop FF1. Specifically, the memory flip-flop FF1 is set to one state after either a Fast Forward or Fast Reverse operation and may only be reset by the activation of the Stop mode. Therefore the tape transport may only go to a Stop mode after a Fast Forward or Fast Reverse mode to thereby prevent damage to the tape.

The logic block L9 receives Fast Forward, Play and Fast Reverse keyboard inputs to control the flip-flop FF2 and the relay K3. The relay K3 is a reversing relay so as to control which one of the motors M103 and M104 is used to provide torque and which one is used to provide brake.

If TM103 = Motor M103 in Torque

TM104 = Motor M104 in Torque

BM103 = Motor M103 in Brake

BM104 = Motor M104 in Brake, then,

TM103 = FR = K3

TM104 = FF + Play + X1 = K3

BM103 = TM103

BM104 = TM104

Logic group L7 in combination with the fast forward and fast reverse inhibit signal I from FF1 and in combination with the play logic L2 and the X1 logic L4 is used to provide an automatic stop feature. For example, if improper operational procedures are followed, wherein any one of four keys if depressed (X1, X30, X60 or X120) after the Fast Forward or Fast Reverse mode, then an automatic Stop mode is initiated as defined below.

I = Inhibit after FF and FR

AS = Auto Stop = (X1 + X30 + X60 + X120) I

In order to stop the motion of the tape, move the tape smoothly at the various speeds, and to hold the tape tight when stopped, the system of FIG. 2 includes dynamic and static braking. This braking is accomplished using a DC current from a current source which is applied to the windings of the AC torque motors M103 and M104. The current is switched from the output of the dynamic brake logic block L9 by the relay K3 to either one of the motors M103 or M104. The brake output circuit includes an emitter follower Q1 as shown in FIG. 2A which is capable of high current output. This current when passed through an AC torque motor causes the rotor to drag due to eddy currents and magnetic hysteresis and the current is of sufficient magnitude to perform high speed braking even for the large reels of tape. A reduced amount of braking current is used during the normal play operation or when the tape transport is in a Stop mode.

The operation of the braking circuit is that one of the motors act as a brake while the other motor acts as a take-up motor to provide that tape tension is always maintained during any mode or during a change from any mode to any other keyboard mode. This insures that the digital clock pulley 100 accurately follows the movements of the tape. Sufficient tension around the clock pulley 100 is maintained during rapid starting, rapid reversing, normal play speeds of X1 through X120, changing speeds from X1 through X120, and during rapid stopping.

The logic blocks L8 and L9 obtain either speed or mode data from the various keyboard entries and logic outputs. In addition, the reel size switch 58 also is used as an input to the logic block L9 to control the amount of braking during different modes of operation. The output of the logic block L9 sets up the following braking conditions where:

BA = Brake to Stop after FF and FR

BB = Brake on X1 speed

BC = Brake on X30 speed

BD = Brake on X60 Speed

BE = Brake on X120 speed

BF = Brake on FF and FR

The amount of braking required during the movement of the tape at the X1, X30, X60 or X120 speed is different due to factors of friction and due to the effectiveness of the hysteresis braking of the motors M103 and M104 and therefore the amount of braking must be varied for each speed. The different braking factors is accomplished by applying different voltages to the emitter follower Q1 shown in FIG. 2A which in turn controls the flow of current to the appropriate motor. The different braking modes provided by the system of FIGS. 2 and 2A are as follows:

In the BA braking mode, maximum DC current flows through the supply motor which is either M103 or M104, depending on tape direction. This maximum DC current causes rapid tape stoppage without losing tension of the tape. The final value of braking exceeds the take-up torque of the take-up motor and therefore the tape stops and remains under tension.

In the BB through BE braking modes different brake values are supplied to the motor M103 to keep the proper amount of tension on the tape. This tension must be sufficient to maintain the drive of the clock pulley 100 and to keep the tape in close contact with the heads such as the trigger head, the high speed head, or the X1 heas as shown in FIG. 2.

In the BF mode a small amount of brake current is allowed to flow through the appropriate motor to maintain the tape tight around all pulleys and especially the clock pulley 100.

The various brake current conditions may be defined as follows:

BA = EA · Z where Z = State after FF or Fr

BB = EB · X1

BC = EC · X30

BD = ED · X60

BE = EE · X120

BF = EF · (FF + FR)

EA, EB, EC, ED, EE and EF equals voltages applied to the emitter follower Q1 to provide current flow through the motor used for braking.

The schematic shown in FIG. 2A includes the emitter follower Q1 driving either motor M103 or M104 as controlled by the relay K3. A rapid braking of the tape occurs when the Stop control amplifier L10 provides current drive to the emitter follower Q1 through diodes CR2 and resistor R1. A capacitor C1 delays this current drive to make the braking smooth and to prevent stretching and breaking of the tape. The amplifier L10 also controls a discharge of the capacitor C1 through the transistor Q2 during any other mode other than the Stop mode so that the Stop mode can be successively repeated. A zenor diode CR3 limits the maximum current during the Stop control.

The brake control logic blocks L11 through L14 are electronic switches which are controlled from the tape-deck speed outputs so as to provide various levels of current to the emitter follower Q1. The reel size switch S1 also controls current level and therefore brake value by switching to a plurality of resistive levels R1, R2 and R3. During the Stop mode or Fast Forward or Fast Reverse modes, the diode CR4 pulls the diode CR1 to a minus voltage such as minus 24 volts and thereby disconnects the speed input and reel size inputs from the emitter follower Q1. During the Play and X1 modes the diode CR4 is back biased to thereby allow the speed input data to go directly to the emitter follower Q1 and control the braking levels of the motors M103 and M104.

The tape head and amplifiers shown in FIGS. 2 and 6, provide accurate and stable reproduction of the dual track recorded signals with recorded frequencies from approximately DC to 100 hertz. The basic recording to be reproduced is made from a prior art standard portable recorder operating at approximately ⅛ inch per second or at a reduced speed such as 1/16 inch per second and the recording is directly on the tape without the use of a subcarrier. This type of recording provides for extremely small reels of tape recording for long periods of time, such as 24 hours.

The ECG computer of the present invention provides for analysis of this recorded tape and requires that signals from the recorded tape be played back at real time (X1) or at increased playback speeds of X30, X60 or X120. Since the tape transport system allows for the speed of the tape to be switched between any of the four playback speeds, the output signal must have the same equivalent signal bandwidth for all playback speeds.

The output signal must also be stable in gain and base line, and be free from transient switching artifacts.

As indicated above, the recorded signals have a frequency bandwidth of approximately DC to 100 HZ. and the amplifier system must reproduce these signals at any speed. This provides for equivalent frequency bandwidths of DC to 100 HZ. at X1, DC to 3,000 HZ. at X30, DC to 6,000 HZ. at X60, and DC to 12,000 HZ. at X120. Playback heads which will provide the proper reproduction of these signals in real time are shown in application Ser. No. 430,704 and reference is made to this application for details of such a head construction.

FIG. 4 illustrates a miniature recorder which may be used to provide the recorded ECG signals of the type disclosed above. The recorder of FIG. 4 includes several advantages over prior art recorders but it will be appreciated that prior art recorders may be used to record a tape with ECG signals, and with this tape reproduced by the ECG computer of the present invention. In FIG. 4, the recorder includes an outer case 120 which has a lid 122 to completely enclose the recorder. A pair of reels 124 and 126 is used to hold the tape during recording. The tape 128 is shown extending from reel 124 to reel 126 and passing over a series of guide members and also over a head member 130 for recording the ECG signals. A capstan drive generally shown at position 132 is used to move the tape at a constant rate. The portion of the recorder described so far is generally the same as that present in the prior art recorders, but the recorder of the present invention also includes additional features.

Specifically, the recorder of FIG. 4 includes a display of 134 which provides for a visual output indication of time. The cover 132 includes an opening 136 so that the time is visible through this opening. The signal input from the electrodes attached to the patient is provided to the recorder through a connector which plugs into connector portion 138. A test output 140 may be used in providing for a test of the operation of the recorder.

An event button 142 is used to actuate a burst signal which is supplied to the tape in lieu of one of the tracks of ECG signals upon command by the patient. Specifically, whe the patient experiences a predetermined event, such as an unusual activity or some sympton which relates to a difficulty in which the patient has been experiencing, the patient is instructed to press the event button, so that the event marker is recorded on the tape. The time display 134 can either be run continuously or may be actuated in accordance with the pressing of the event button. In either case, after the patient presses the event button, he may also make a log of the time that the event occurred, plus a description of the event. Upon play back, the event mark on the tape will be automatically detected during auto-scan so that the tape can be slowed down to real time with a real time write out of the ECG signals corresponding to the event. The ECG signals may now be correlated with the log notation of the patient.

FIG. 5 illustrates a block diagram of the event mark pulse generator which is included in the recorder shown in FIG. 4. FIG. 5(a) are waveforms which are used to explain the operation of the block diagram of FIG. 5.

The event mark pulse generator of FIG. 5 is designed to provide a burst of symmetrical square waves of a precision amplitude. For example, the square waves may be at a frequency of 8 HZ. and have an amplitude of 2.0 millivolts peak to peak. The burst produced by the generator provides three basic function. First, the burst is used to automatically mark the tape upon the patient actuating the event mark switch 140 which marking of the tape correlates with either symptoms or activities experienced by the patient. In addition, as indicated above, the patient may keep a log of the time of day at which he activated the event mark switch and may also indicate the nature of the event. Secondly, the burst provides a signal on the tape with characteristics sufficiently dissimilar to the ECG signals, so as to be reliably detectible by an electronic detection system in the ECG computer. This detection then provides for the automatic real time write out during the auto-scan cycle. Thirdly, the burst may provide a means for verifying the system calibration throughout the recording period which may be used to assure system accuracy.

The event mark pulse generator of FIG. 5 provides the precise burst of pulses as shown in line E of FIG. 5(a) and specifically, this burst may be a precise 2 millivolt peak to peak 8 HZ., 8 cycle pulse. This type of a pulse will insure reliable detection in the presence of a wide variety of ECG and artifact characteristics.

The pulse generator specifically consists of a stable, fixed rate clock source 144 which produces an output signal as shown in line A, FIG. 5(a). The clock signal is passed through a gate 146 and clocked into a counter 148 which divides the signal down. The clock can have any particular frequency and for example, may be at 256 HZ. The counter 148 divides this frequency down to an output of $2^P$. The $2^P$ output is twice the number of pulses desired in the burst and in our specific example would be a 16 HZ. output. This 16 HZ. output is passed to an electronic double throw single pole switch 150, which is used to interrupt the normal signal path which comes from an amplifier path 152. The normal signal path is from the amplifier 152, through the switch 150, and to a head modulator 154 to drive the recording head.

When the switch 150 is in position to record the burst, an 8 HZ. output is applied through a precision gain scaling network 156 to established burst and amplitude. The switch 140, which may be activated by the patient, is used to initiate a pulse through a capacitor 158. Specifically, depressing the switch 140 creates the differentiated pulse as shown in line B of FIG. 5(a) which resets all of the counter inputs to logic zero.

The $2^P$ output of the counter which is the 16 HZ. output is inverted by invertor 160 to provide an enabling input to the clock input of the counter through the gate 146. The 8 HZ. output or the $2^N$ output as shown in line D of FIG. 5(a) is selected to be the pulse frequency desired. The clock frequency M which as indicated above, may be 256 HZ., is selected as a binary multiple of the desired pulse frequency. When P number of pulses have been generated, the $2^P$ output returns to a logic "1" which is a high voltage level, thus disabling the clock input and preventing further pulse generation until the next switch 140 activation.

The counter output ($2^P$ or 16 HZ.) transfers the electronic switch 150 from the normal ECG position, to the burst position during the logic "1", thus preventing interference of burst signal by the ECG signal and improving playback decoding reliability. Specifically, the switch 150 is inserted between the ECG amplifier 152 and the head modulation driver 154 is referenced to the recording circuit ground by a bias resister 162. In addition the gain scale network is used in order to provide pulses which are bi-polar and symmetrical with respect to the ECG base line to prevent any DC component from altering the base line after termination of the burst during playback.

Turning now to the reproduction of the ECG information, the output from the real time head 208 is applied to a sensitive amplifier 164, as shown in FIG. 6, and the amplifier is followed by the 66 db integrator 166. The loss from the integrator 166 must be made up by the amplifier 164 in order to insure a sufficient output signal from the integrator.

A separate high speed head 204 is used for the reproduction at X30, X60 and X120 playback speeds. This high speed head 204 may be a conventional stereo playback head which has a frequency response of 3 to 12,000 HZ. The frequency response necessary for the X30 playback, which is equivalent to 3 and ¾ inches per second is 3 to 3,000 HZ. The frequency response at the X60 playback, which is equivalent to 7½ inches per second, is 6 to 6,000 HZ. and the frequency response for the X120 playback, which is equivalent to 15 inches per second, is 12 to 12,000 HZ.

The high speed head 204 shown in FIG. 6 supplies its output signals to the high speed amplifier 168 which is a DC amplifier having a response from DC to 15,000 HZ. This amplifier has its gain programmed in accordance with the tape speed signal provided from the system of FIG. 2. The output from the amplifier 168 is coupled to a programmed integrater 170 which intergrates the output signal to give a flat response from 3 to 12,000 HZ. As shown in FIG. 6, a plurality of switches control the integrater 170 in accordance with the tape speed and a frequency programmer controls the frequency response of the integrater in accordance with the tape speed. Typically, the amplifier 168 is programmed for gain for the different gain outputs from the head at the three tape speeds. Frequency programming of the integrater 170 for the three tape speeds in the ratio of 1, 2 and 4 for the speeds of X30, X60 and X120 is accomplished by switching the value of the capacitator CF. The value of the integrating circuit 170 may also be switched in the ratio of 1, 2 and 4 to control the integrating time constant at the different speeds.

The integraters 166 and 170 are placed at the output of the amplifiers 164 and 168 to insure that all noise picked up from the heads or amplifiers is then attenuated by these integraters. This will give an extremely noise-free output without any 60 HZ. interference. The output from the integraters 166 and 170 are connected to high pass filters 172 and 174 so as to remove any DC component which may have been provided by the amplifiers 164 and 168. The output from the high pass filters 172 and 174 may then be switched using the switch S2, and the switch S2 may be an FET electronic switch so as to provide a transient free base line to insure that all subsequent components in the system are not disturbed. As indicated above, the switch S2 may be an electronic FET switch which may be digitally controlled in accordance with the tape speed so as to provide switching between several modes. These modes may be the X1 playback speed mode, the high speed mode, and a switching to ground mode. For example, during Fast Forward, Fast Reverse, or Stop, the amplifier output is switched to ground to prevent any transient signals from showing on the output.

As indicated above, and as shown in FIGS. 2 and 6, the tape transport uses two playback heads 204 and 208 to achieve the real time playback at X1 and the high speed playback at X30, X60 and X120 times recorded time. In addition to the use of two playback heads to achieve optimum fidelity to the recorded signal for the various playback speeds as explained above, the use of two heads also allows for the viewing of the ECG signals at high speed in a superimposed display on the oscilloscope 10 and a subsequent slowdown to the X1 speed to provide a paper writeout on the paper writer 12 of the same information previously viewed on the oscilloscope. FIG. 7 illustrates the tape loop including an adjustable time delay loop portion to allow for the operator of the ECG scanner to provide for the proper manual paper writeout in accordance with the previous high speed viewing and in accordance with the reaction time of the operator. The automatic real time paper writeout will be described at a later portion of the specifications, but the ability to provide the rapid switching between different speeds will be described with reference to the manual actuation by an operator.

The manual paper writeout in real time after viewing at high speed is possible since the direction of tape flow is from right to left. Specifically, the magnetic tape from the supply reel 200 is guided by a plurality of tape guides to pass over a trigger head 202 and the high speed head 204. The tape is then guided by guide members to a variable delay loop portion 206. The tape is then guided by guide members to pass over the X1 head 208 and around the optical encoder pulley 100 to be received by the take-up reel 210. The variable delay loop 206 is used to vary the time before the tape is received at the X1 head 208 after being viewed by the high speed 204. The delay loop 206 provides a variation in time from a minimum value in accordance with the position of the variable delay loop. The delay loop 206 includes a guide roller 212 which can be adjusted along a vertical path in accordance with the movement of the guide roller by a guide arm 214. A clamping knob 216 is used to clamp the arm 214 and roller 212 in the desired position. A pointer member 218 extends from the guide arm to give a visual reading of the delay time.

The adjustment of the position of the guide roller 212 is variable to enable different operators to adjust the quantity of ECG signals that are written out prior to the desired portion and also the compensate for differences in operator reaction time. For example, the operator may be operating the Electrocardioscanner at X120 playback speed and may be viewing the superimposed image on the oscilloscope. The operator can see a single abnormal ECG beat, such as a PVC, since this will produce a characteristic visual and audio deviation from the normal superimposed image. Without hesitation, the operator presses the desired auto ECG key to change the speed to real time and to activate the paper writer. Because of the delay loop, the ECG complex having the PVC and some previous quantity of ECG complexes will be written out by the paper writer.

Since different operators may desire to view the superimposed image at different ones of the high playback speeds, such as either the X30, X60 or X120 speeds, the time required for the tape to move from the high speed head 204 to the real time head 208 varies in accordance with the speed of playback. Specifically, the delay time varies from 2 seconds to 0.5 second at the different speeds with the variable guide member 212 adjusted to provide for the minimum delay loop. The delay loop 206 when adjusted at its maximum position doubles the times before the tape passes from the high speed head 204 to the real time head 208. It is to be appreciated that when the operator switches from high speed playback to low speed playback, the tape movement is quickly reduced, so that the actual time before the tape previously viewed at high speed reaches the low speed head 208 is considerably in excess of the time periods given above. For example, if the tape speed could be instantaneously reduced to real time after the tape has passed by the high speed head 204, the minimum time the tape would take to get to the real time head 208 would be approximately 60 seconds. The variable delay loop means when adjusted to its maximum position doubles the time to 120 seconds. This allows the operator to write out a significant quantity of the ECG complexes prior to the irregularity, so as to help in the analysis of the medical problem. Since the onset of the irregular ECG beat may in itself contain valuable information.

The use of the variable delay loop 206 is important since the operator does not have to rewind the tape to write out a complex that he has already reviewed. As indicated above, the delay loop 206 also allows for different operator reaction times and these times would be different for different operators and would be different for the same operator as his proficiency changes due to training and experience.

The method of scanning at high speed and superimposing ECG complexes on an oscilloscope has been described above with reference to U.S. Pat. Nos. 3,215,136 and 3,718,772 which have issued on the dual track method and the single track method. The superimposed ECG presentation on the oscilloscope may be achieved using a trigger signal from the trigger head 202 which starts the cathode-ray tube trace before the P wave portion of the ECG complex. The position where the waveform starts relative to the start of the trace is variable to allow viewer preference or to make up for any inaccuracies associated with the trigger system. In addition, since the playback operates at speeds of X30, X60 and X120, the time between the ECG complexes will vary with the playback speed. In order to insure that the complex does not change in shape or duration, the display time base speed varies with the tape speed. The time delay at the beginning of the trace also varies with playback speed to insure that the overall ECG complex remains superimposed with changes in tape speed. This general system for triggering is described in detail in above-referenced U.S. Pat. No. 3,718,772 and reference is made to this patent for full details. In addition, application Ser. No. 430,704 describes a specific system which may be used for triggering and response is made to this application for additional details of a triggering system.

The recorder, as shown in FIG. 4, generates a signal burst as shown by the block diagram of FIG. 5 each time the event button 142 is pushed and as indicated above, the signal burst consists of a train of pulses as shown in line D, of FIG. 5(a) over a 1 second period. This signal burst interrupts the ECG being recorded on the recorder on one of the tracks. On playback, the tape may be scanned at X30, X60 or X120 real time and passes the high speed head 204 as shown in FIG. 9.

The output from the head 204 is amplified by amplifier 220 and the signal normally has the appearance of a differentiated signal so that it provides for a pulse at the beginning and end of each one of the square wave components of the burst. This differentiated signal is shown as an input to a comparitor 222 which also includes filtering. The comparitor 222 outputs pulses above a certain level and the output of the comparitor 222 is applied to a counter 224. The comparitor 222 may also include an inhibit input from a cycle so as to allow for the ECG computer to cycle the trend analysis completely to the end and then reverse this tape to the beginning and the cycle through to detect the events.

The output from the counter is passed through a pulse train interval detector 226 and then through a pulse width detector 228. The pulse train interval detector 226 may be a one shot to insure that the train of pulses occur in 1 second. The pulse width detector 228 may also be a one shot to determine that the pulses are of the proper width. The counter 224 may be a counter that provides an output when there is a pulse train having pulses between 8 to 11 counts. In this way the coding consists of counting a pulse train to see if it has between 8 and 11 counts, determining if this pulse train occurs in a time period equivalent to a 1 second train at real time and then determining if the pulse width is equivalent to the recorded pulse width. After each of these conditions is determined to be true, then a burst-out signal goes to a delay circuit 230 to start a counting process.

The burst-out signal passes through the switch 92 as shown in FIG. 1(a) to control whether the ECG computer during auto-scan will be responsive to the events which have been marked on the tape by the patient. In addition, the input to the delay circuit 230 may be from one of a number of inputs shown in FIG. 9 to be controlled by switches 86 through 96 which are generally the switches shown in the computer auto-write section 72 in FIG. 1(a).

The delay circuit 230 counts approximately 96 encoder clock pulses for the switch 76 in the half speed position, or 48 encoder clock pulses for the switch 76 in full speed position, which count indicates that the tape has moved 96/16 inches since the tape moves either 1/16 or ⅛ inch for each pulse in accordance with the position of the switch 76. The optical encoder which is disclosed in greater detail in FIG. 2 is coupled to the tape since the encoder is driven by the pulley 100 and the shaft 240. The count by the delay circuit 230 starts after a burst has been received or a signal representing an event is coupled through switches 86 through 96 and applied to the count start input of the delay circuit 230.

After a count of 96 or 48 counts, in accordance with the position of the switch 76, the signal that was detected at the high speed head 204 shown in FIG. 2 moves towards the X1 head 208 and is controlled to slow down to real time at a position approximately 1 inch from the head gap of the X1 head 208. Specifically, the tape is controlled to slow down from any of the preselected high speeds to the X1 real time speed which is at ⅛ inch per second. This slow down is provided by an output from a timer 232 which puts out an X1 tape speed signal to control the tape deck and override any of the original tape deck's speed control signals. The particular period of time that the tape is written out at the X1 real time speed is determined in accordance with the position of the switch 84 and may be in a specific example, 15 seconds, 30 seconds or 60 seconds of real time write out.

At the end of the real time write out, a tape deck speed memory 234 is activated by a signal from the timer 232 to return the deck to the original high speed of either X30, X60 or X120. The memory circuit which may be a flip-flop memory latch is activated from the original tape speed commands to remember at which speed the tape deck was travelling and then to return the tape deck to this speed after the period of real time write out.

If additional real time signal write out is required to the period prior to the event signal, the delay loop shown in FIG. 7 may be extended to write out up to an additional 60 seconds of real time. Normally, the position of the delay loop would be at the minimum position, but this minimum position can be adjusted up to the additional 60 seconds of real time write out.

FIG. 9(a) illustrates the typical write out of real time information during auto-scan with the delay loop in the minimum position, and with approximately an 8 second write out prior to the event, and with an adjustable write out for the total event from 15 to 60 seconds. The 1 second burst is shown in the middle, but normally, this is only present in one of the tracks of write out and only if the auto-scan real time write out was activated by the burst signal. If the auto-scan real time write out is actuated by the detection of preselected events present in the ECG signals, this burst would not be present.

In order to provide for a digital clock in accordance with the tape travel, a clock drive mechanism as shown in more detail in FIG. 10 is used. In FIG. 2 and in FIG. 7, the clock drive pulley 10 was shown to be part of the tape path and this pulley is maintained in constant engagement with the magnetic tape as provided by the tape tensioning features described above. The pulley 100 provides a drive to an optical encoder which in combination with the pulley provides for the basic clock drive. Since these mechanical elements are controlled by the movement of the magnetic tape, they are generally designed to be lightweight and to have a relatively low inertia.

A shaft member 240 is coupled from the drive pulley 100, and includes a slotted disc 242 positioned at the end of the shaft, so that the slotted disc 242 moves with movements of the drive pulley 100. The disc may have 48 slots per revolution and a movement of the magnetic tape is translated into a rotation of the disc 242. A pair of light sources 244 and 246 which may be LEDs provided light energy directed towards the disc and specifically to pass through the slots in the disc 242. A pair of light detectors such as photocells 248 and 250 detect light output from the light sources 244 and 246. The diameter of the pulley 100 is adjusted so that each 1/16 inch of tape travel causes a signal output from each of the photocells 248 and 250. In addition, the photocells are spaced apart so that one photocell produces an output signal 90° in phase ahead of the other so as to indicate the direction of tape travel. This can be shown in FIG. 10(a) where the output of photocell 248 is shown in solid line and the output of photocell 250 is shown in dotted line.

The output signals from the photocells 248 and 250 are applied to amplifiers 252 and 254, which may be conventional buffer gates, so as to provide for amplified square wave pulses to be directed to a time clock. Since an output signal for each 1/16 inch of travel is provided at real time playback, an output signal each second is provided to the digital clock. Referring now to FIG. 11 the output of the optical encoder and input to the digital clock is shown to be square wave pulses having a 90° shift.

The digital clock system, shown in FIG. 11, provides a visual output clock as shown at position 16 in FIG. 1. In addition, the digital clock provides output information which is used in the paper writer section by printer mechanism 14 to provide for printout of the digital clock information. As indicated above, the optical encoder measures tape length in 1/16 inch units and the digital clock system converts this to changes in time of day either increasing or decreasing. This is accomplished at the various playback speeds in addition to the fast forward and fast reverse speeds. A plurality of preset inputs 256, 258, and 260 allow the presetting of each digit to any number so that the start time of the digital clock can be correlated to the start time of the recording which is to be analyzed.

The digital time clock keeps track of the recorded time on a 12 hour basis and provides visual time of day outputs as shown by indicators 262 through 268. In addition, a pair of output indicators 270 and 272 provide a visual indication of AM or PM so as to cover a full 24-hour day.

The digital clock is operated in a bidirectional mole either counting up or down and controlled by an up-down logic gate 274 and with each input pulse proportional to one second. Logic gate 274 determines which signal A or B comes first and then actuates standard up-down counters to count in the proper direction. The digital clock also provides output BCD signals of each digit in sequence which relate to the visual indication and to the AM-PM. These output command signals may either be controlled from internal timing controls such as an event or a marker control, or from an external input. For example, at a particular event or at a particular preselected time, a printout of the time may be provided by the printer 14 on the paper. This printout would be a typical digital printout such as 11:59 AM.

In addition to the printout of time, the digital clock provides additional sequential information to be printed immediately after the printout of the time. For example, the arrhythmia computer provides digital information as to the number of VEs and SVEs and in addition to the printout of time, the number of such VEs and SVEs may be printed out. This typically occurs when the tape transport and display operates in the trend mode. The typical printout is as follows: 12:00 AM 032 060. The printing of the numerals after 12:00 AM occurs sequentially, one at a time, after the AM has been printed.

The three numbers represented by 032 indicate the number of VE beats and the three numbers represented by 060 indicate the number of SVE beats. Both of these numbers are provided from the arrhythmia computer portion of the system and the time of printing is controlled by the digital clock.

As indicated above, the digital clock controls a printout by the paper writer of the time when operated in a trend mode. At that time, the paper is moved at a relatively slow speed. The paper writer may be of that heat stylus type and would use a heat stylus located in the upper portion of the paper writer 12 and as represented by heat styli 276 and 278 as shown in FIG. 1. The digital printer 14, shown in FIG. 1, has a mechanical separation from the heat styli 276 and 278 and because of this mechanical separation, the visual printout would normally have time errors.

Specifically, since the digital printer is ahead of the writing styli, the writing styli provides the writing of information correlating to a particular time on the recorded tape and the digital printer is considerably ahead of the writing styli. At low paper speeds, such as in the trend mode, the time error is considerable. As an example, the separation between a print wheel, which is part of the digital printer 14, and the writing styli 276 and 278 may be on the order of 8 centimeters. At a paper speed of 1 millimeter per second, this would represent a time error of 80 minutes. The digital clock shown in FIG. 11 corrects for this time error for paper speeds of 1 millimeter per second or 2 millimeters per second, which correspond to the tape playback speeds of X60 or X120. Generally the tape playback speeds of X60 or X120 are the only ones used in the trend mode. Specifically, the correction for the time error is generated from the signals which are used to provide for the digital display.

During a trend printout, the time is digitally printed with this time correction of 80 minutes. When the data written by the styli 276 and 278 gets to the area of the printer 14, the correct time is then printed along the edge of the paper. The method of achieving this printout is greatly simplified in that only one set of components is used to drive the digital display and then this same BCD data as displayed is modified to provide a correct printout of the time.

As shown in FIG. 11, the up-down control 274 is driven by the output pulses from the optical encoder which corresond to a one-second rate for each ⅛ inch of tape. Depending on the direction of tape travel, one of the pulses always leads the other, so as to provide for the up-down control producing the appropriate output pulses to drive the dividers 280 through 286 and the drive 288, which controls the AM-PM indication.

The display indicators 262 through 272 may be standard LED or Nixie tubes and displays four numbers such as 11:59 to indicate the time and also the AM-PM indication. Since the output of the up-down control 274 corresponds to a one-second rate, the first divider 280 divides by 60 to change the one-second rate to minutes and to drive first display 268. The succeeding logic dividers 282, 284 and 286, convert the minutes to tens of minutes by dividing by ten, to hours by dividing by six and to tens of hours by dividing by 10. Finally, the divider logic 288 provides an output indication of AM or PM at 12 o'clock.

The first three least significant digits may be changed any time by controls 256, 258 and 260, so as to initially set the indicators and dividers to a desired time which corresponds to the start time of recording on the recorded tape. The most significant digit is controlled by the set switch 256, so that this set switch not only sets its own indicators 264, but at the change from 9 to 0, the most significant digit is changed from 0 to 1, and when the displays 264 and 262 go from 11 to 12, the AM-PM lamps are also activated.

During the X1 playback mode, the digital time is normally printed on the paper writer by the unit 14 from either an external push button command or at the actual start of the paper writer. These two inputs are shown provided to the data selector multiplexer 290 which includes counters and gates to look at each BCD number in sequence, one at a time. In the X1 playback mode, the actual time of day from the clock output drivers 280 through 286 are connected to a latch multiplexer 292 via the printer trend mode correction unit 294. The latch 292 is formed of flip-flops to hold the digital value of the display in BCD form. The unit 294 is formed from gates which are sampled by the clock 296 and then outputted into the latch 294. The paper speed from the trend or X1 signals is inputted to control the take off point, with the correction of 80 minutes when desired. The printer trend mode correction is controlled during the X1 playback mode to merely pass on the clock outputs to the latch multiplexer 292. The data from the latch 292 and multiplexer 290 is multiplexed out in sequence at a rate determined by the data sequence clock 296. The clock 296 is of standard design having an output pulse rate controlled by the speed of the paper writer so as to output the printer at a slow rate on trend or at the faster rates of 25 or 50 mm/s on X1.

In the X1 operate mode, the paper writer is driven at a relatively high speed and the time differential between the writing of the data by the heat styli 276 and 278 and the time printout by the unit 14 is relatively small. This time error is on the order of 4 to 5 seconds and no time correction may be necessary in this mode. It is to be appreciated, however, if such a time correction is desired, it could be provided by conventional means by using a time delay in the printout of the information. The output from the multiplexer 290 is BCD data, and this data is coupled through a BCD interface 298 to the external digital printer 14, where generally one digit at at time is printed. The print commands to the printer 14, which correlate to the BCD data, is supplied by the data sequence clock 296. In addition, print inhibit signals are supplied to and from the data sequence clock. During the X1 playback mode the data dequence clock is reset to start over, after the AM or PM is printed.

With the exception of the time of printing by the digital printer 14, the digital time clock operates the same as the X1 speed and at faster tape transport speeds. During X60 or X120 trend, analysis of the ECG complexes is provided and output signals reflecting this analysis as a trend is written by the paper writer. This output trend data consists of analog heart rate, analog ST level, event marks and the digital printout of time and number of VEs and SVEs, both of which are determined by the arrhythmia computer. As described above, a time correction must be made during the trend mode to correct for the mechanical spacing between the heat stylus and the digital printer. Specifically, the time that is printed by the digital printer 14 during the trend writeouts is corrected by 1 hour and twenty minutes. This enables the heat stylus writeout to proceed to provide writeout with the paper moving at a slow rate and with the correct time printed along the paper edge.

In order to provide this time correction of one hour and twenty minutes, the printer trend mode correction unit 294 provides the following operation. The input data proceeds into the unit 294 until the two least significant bits reach 59. After 59 is changed to 00 in unit 294, but before the next hour digit is changed, the clock data from the unit 294 is sequenced at a high rate into the latch 292 and is then inhibited from further change for an hour. The latch 292 therefore receives the time as 11:00 AM, rather than 12:00 as displayed by the display elements 262 through 268. A twenty minute delay in printing is then initiated by waiting until a 2 occurs in the second least significant digit, such as at 12:00 AM on the digital display, before the printer 14 is commanded tp printout the information held in the latch 292 which would be 11:00 AM. The printing of the time is then followed by an event mark as shown in FIG. 12.

After the event mark, the arrhythmia computer output would supply information to be printed at positions following the time as explained above. The output circuitry of the arrhythmia computer is connected in parallel with the digital time clock to supply information to the digital printer. The data sequence clock 296 is used to control the sequential printing from the arrhythmia computer of the information supplied by the arrhythmia computer.

In FIG. 13, is shown a typical auto-scan chart write out, including trend information which would be identical to that shown in FIG. 12, but additionally including periodic write out of real time information in response to inputs from the burst detector, arrhythmia computer, ST computer or heart rate computer. Normally, during the auto-scan cycle, the trend data of heart rate and ST level is written out in a normal way as shown in FIG. 12. ECG write out at the real time speed during this time is inhibited. At the end of the tape an automatic reversal is initiated to the beginning of the tape and after a slight delay, the tape then scans at the original fast speed.

The initial write out is shown in the left-hand portion of FIG. 13, identified as portion 300 and is indicated to be Trend Cycle 1. During the second cycle, inputs from the burst detector, arrhythmia computer, ST computer or heart rate computer may activate the real time write out mode for a predetermined time of 15, 30 or 60 seconds. For example, portion 302 of FIG. 13 shows one real time ECG data write out and identified as ECG Data Cycle 2. Following this typical real time write out, the trend data is again plotted to show the heart rate and ST level in the normal fashion, and this is shown at 304 of FIG. 13 and is identified as Trend Cycle 2. If the event burst is again detected, or if one of the other external inputs from the arrhythmia computer, ST computer or heart rate computer is detected, the system will again write out real time ECG data. This is shown at portion 306 of FIG. 13 and identified as ECG Data Cycle 2 and would have the same period as the previous real time write out. During the write out at real time, the time of such write out relative to the time at which the recording was made, may be printed to show the time of the unusual activity. The process of writing out the trend information with periodic write out of real time ECG information, in accordance with the detection of an unusual occurrence, may be repeated many times during the auto-scan write out of the information.

At the end of the auto-scan write out, the tape may again be reversed to the beginning, but at that time, the tape stops. If it is desired, a repeat of the auto-scan cycle may be initiated by actuating any of the high speed modes, and the parameters which control the real time write out may be changed.

Referring now to FIGS. 8 and 8(a), the system for providing the auto-scan and auto-stop cycles is shown together with a chart illustrating the cycling of the tape auto-scan or auto-stop. In FIG. 8 a light source 308 and light detector 310 provide an end-of-tape signal. The light source and light detector may be positioned as shown in FIG. 7. For example, the end of the tape may include a transparent portion to allow the passage of light from the light source 308 to the light detector to provide the end-of-tape signal and this signal may be used to stop or to reverse the tape drive.

The switches 80 and 82 are used to control the auto-stop and auto-scan cycle and in combination with a logic block 312 provide for the following sequence of operations. First, if only the auto-stop switch 80 is closed, the tape is controlled to stop at either end of the tape. The length of the transparent portion of the tape may be sufficient so that the light source 308 and light detector 310 will detect the tape being at either end no matter what direction the tape has travelled.

When both switches 80 and 82 are closed, the logic block controls the tape trnaport system over two complete cycles, or four half cycles as shown in FIG. 8(a). It can be seen in FIG. 8(a) that the first cycle, which consists of two half cycles provides for a continuous high speed trend playback to the end of the tape in the forward direction and then a reversal of the tape back to the beginning of the tape. The second cycle is a high speed playback with periodic reductions of speed to real time write out in accordance with the detection of specific events within the characteristics of the ECG complexes. This continues to the end of the tape and with a reversal to the beginning of the tape and a final stop of the tape.

At the start of the auto-scan cycle, a cycle counter 314 is reset to zero by a reset signal from the speed commands shown in FIG. 2. As indicated above in the auto-scan operation over the first half cycle shown in FIG. 8(a), the tape runs at the commanded high speed and trend signals are outputed to the paper writer. The trend cycle output also goes from the cycle counter to the paperwriter to control the paper writer at the proper speed. The cycle counter 314 also provides an output signal to inhibit the playback decoder shown in FIG. 9. At the end of the first half cycle, the end-of-tape sensor provides a signal to the logic block 312 to control the cycle counter 314 to reverse the tape drive to the beginning of the tape and when that has occured, to start the second cycle to drive the tape at the same high speed as previously commanded.

During the second cycle of auto-scan, the inhibit input is released from the playback decoder shown in FIG. 9 to enable the playback decoder to detect event signals. The ECG computer then provides a trend output similar to that in the first cycle. However, if the playback decoder detects an event, the playback decoder provides a control signal to the motor drive logic to control the motors to provide playback at real time for a predetermined period of time, also provides a speed signal which is supplied to the paper writer to control the speed of the paper writer to write out the ECG signals in real time for the particular event. The periodic real time write out may occur any number of times in accordance with the detection of individual events and with each period of real time write out interspaced with trend data. The motor drive logic is shown in FIG. 2 and the details of the paper writer is described in another portion of this specification. At the end of the auto-scan cycle, the end-of-tape sensor again signals the end of the tape and the motor drive is so as to rewind the tape to the beginning. When the tape has been completely rewound, a final stop command from the cycle counter stops all functions.

Turning now to the details of the two channel paper writer 12 shown in FIG. 1, this paper writer has provision for write out of two channels, using styli 276 and 278 in addition to the digital print out from digital printer 14. The write out with the two channel styli 276 and 278 may be for either two channels of ECG signals reproduced in real time and with the paper moving at a relatively high speed, or for write out of two channels of trend information with the paper moving at a relatively low speed. In addition to the two styli 276 and 278 to write out the dual channel information, three event markers, as shown at positions 400, 402 and 404 in FIG. 1 and FIG. 14, provide marker indications to indicate the occurrence of particular transient data.

As described above, the digital printer 14 is also used to print sequentially a series of numbers and AM or PM along one edge. FIGS. 12 and 13 illustrate the typical two channel recording when the electrocarioscanner of the present invention is used to provide a trend chart or auto-scan. The trend portion of the charts in FIGS. 12 and 13 shows the average heart rate in the upper portion of the chart and the ST level on the lower portion of the chart, all with relation to time. Along the upper edge of the chart the time is printed out on an hour-by-hour basis with an AM or PM indication, followed by a time marker produced by the event marker 400 shown in FIG. 14. The event marker is then followed by a three digit number representing the number of VEs which have occurred in the next hour. This is followed by the number of SVEs which have occurred in the next hour. As previously described, the printing of the time is delayed for an 80 minute period to compensate for the time error in the movement of the paper, so it is possible to have the information relating to the PVCs and STVs occurring in the next hour and to have this printed immediately following the time indication.

At a central position in the chart, the event market 402 shown in FIG. 14 produces event marks which indicate that the VEs and SVEs have exceeded a predetermined number of VEs and SVEs per minute. This predetermined number is preset and is adjustable from the front panel of the electrocardioscanner by switch 46 shown in FIGS. 1 and 17. At the bottom edge of the chart, an event mark is produced by the event marker 404 and such an event mark indicates that the number of VEs and SVEs per minute have exceeded a present value.

The heat styli 276 and 278 are controlled by galvanometers 406 and 498, and the input signals to drive these galvanometers come from the tapedect. Specifically, signals used to drive the oscilloscope applied to switching amplifiers 410 and 412 shown in FIG. 14. These switching amplifiers 410 and 412 are digitally controlled and accept more than one input and provide output signals in accordance with the switching logic. For example, the trend input signals are also applied to the amplifiers 410 and 412. The control of the switching amplifiers 410 and 412 is provided by logic blocks 414 and 416, which include standard gate logic. The logic blocks 414 and 416 may be identical and consist of gates and flip-flops which output four logic states to control the gain of the programmable amplifier 410 to four different gains. The logic blocks 414 and 416 control the ECG sensitivity for the push button controls 36 and 38 when the print out is ECG complexes in real time. In addition, a trend input control signal is applied to the logic blocks 414 and 416. When the trend input control signal provides information that the trend program is to be printed, the gate logic 414 and 416 control the amplifier switches 410 and 412 to provide as output signals, to the galvanometers 406 and 408, the trend signals.

The control of the paper drive is in accordance with the push buttons 40 and 62 shown in FIG. 14 and in FIG. 1. If the paper writer control section 62 is activated to control either ECG or auto-ECG, then the output speed is determined by the controls 40 as applied to digital logic circuit 418. The circuit 418 consists of standard gates and flip-flops to output three logic states. The logic circuit 418, in turn, provides control to digital logic circuit 420 to control the motor speed at three different values. The circuit 420, which consists of standard gates and flip-flops is also controlled by the vour push buttons 62 to give a total of four different motor speeds and an event output state. A motor drive 422, which consists of relays, is driven by circuit 420 and in turn controls two motors 424 and 426, each at two speeds.

The combination of the particular speed from controls 40 and the ECG or auto-ECG selection from controls 62 provides a control of the motor drive 422 to control a motor 424 to drive the paper at the higher speeds. If the trend mode is selected from the group of push buttons 62, then the digital logic circuit 420, as modified by the X60 and X120 tapedect speed, is used to control the motor drive 422 and ultimately the motor 426 at the appropriate speed in accordance with the tapedeck speed. Specifically, the motor 426 at a tapedeck speed of X60 would provide a paper drive of 1 millimeter per second. At the tapedeck speed of X120, the paper speed is 2 millimeters per second so as to keep the times scale on the trend chart of 1 millimeter equal to 1 minute. The paper drive speed using motor 424 is either 25 or 50 millimeters per second in accordance with the control provided by the keyboard buttons 40.

The digital logic circuit 420 provides a further control of an event marker when the button marked Event in the group of buttons 62 is activated. This, however, occurs only when the paper writer is in the ECG mode. Also, each time the tapedeck starts in the S1 mode, the digital logic circuit 420 provides an output to the event markers through the event stylus driver 428.

The paper writer also includes the digital print out mechanism 14 which is a one character impact printer that is sequentially activated in a conventional manner to print a series of numbers along the side of the paper. Input to this printer may be from the digital time clock as described above and from an arrhythmia computer to achieve the print out as shown in FIG. 13. The rate of print out is varied for the different paper speeds to provide a constant spacing between the characters. The digital printer is controlled by the printer electronics 430 which as indicated above, receives information from the digital time clock and from the arrhythmia computer.

Three event styli 400, 402 and 404 are driven from the event stylus driver 428 which receives two inputs from the arrhythmia computer to provide representation of PVS and STV events, and also receives an event input from the digital control logic 420 as described above.

As shown in FIGS. 12 and 13, the typical trend and auto-scan write outs provide a dual channel write out of heart rate and ST level. The paper writer system as shown in FIG. 14 when controlled in the trend mode, provides such a trend chart. The heart rate channel may be calibrated with a heart rate scale from 0 to 250 beats per minute, and the ST channel may have a scale from −5 millimeters to +5 millimeters. These scales will generally cover all of the ranges encountered in ECG monitoring. The presentation of this dual channel trend information is coupled to the paper writer as shown in FIG. 14 and is specifically coupled into the switching amplifiers 410 and 412 and is controlled to provide output signals to the galvanometers 406 and 408 which in turn control the heat styli 276 and 278. The actual trend information is produced by two module sections 432 and 434 in FIGS. 1, 15 and 16.

FIG. 15 illustrates a block diagram of the heart rate trend computer section 434. The heart rate trend computer includes inputs relating to the two tape trend speeds of X60 and X120 so as to control the output signal for these two speeds. A trigger signal produced by a trigger system such as shown in application Ser. No. 430,704 is also provided as an output. This trigger signal from the trigger head is conditioned to eliminate artifact noise. The trigger signal and the speed signals are applied as inputs to a pair of one shot multivibrators 436 and 438. These one shots generate a narrow pulse for each trigger input signal. The width of the output pulses from the one shots are adjusted to be in direct relation to the speed input. Only one output pulse from either of the one shots 436 or 438 is coupled to a low pass filter 440 depending upon the speed at which the tape transport is moving.

The low pass filter provides a pulse averaging of the input signal so that the output DC level of the low pass filter 440 is in a direct relationship to the input heart rate. The different pulse widths from the one shots 436 and 438 insure that the amplitude of the output signal from the filter 440 is related to heart rate and not playback speed. The switch 442 varies the filter time constant so that the output response time of the filter 440 may be varied over a range of beats before the change in rate is fully and accurately displayed on the trend chart. The output from the low pass filter 440 is passed through an amplifier 444 to bring the level of the EC signal to a sufficient level to drive the galvanometer 408 as shown in FIG. 14. A variable potentiometer 446 may be used to adjust the DC level so as to control the position of the DC trace.

The heart rate trend computer section also includes a low heart rate and a high heart rate detector section. This detector section includes a pair of potentiometers 435 and 437 each coupled between a reference voltage input and ground, to provide potentiometer outputs which are applied as inputs to a pair of comparitors 439 and 441. The outputs from the potentiometers are adjustable so as to control the level of detection for the low heart rate and the high heart rate. The comparitors also receive as input signals, the output from the pulse averaging low pass filter 440 which represents the actual heart rate. When the comparators 439 or 441 detect the presence of a low heart rate or a high heart rate, output signals from the comparators are coupled to one of the external inputs in the playback decoder of FIG. 9. Specifically, the outputs from the comparators are coupled through individual ones of the switches 86 through 96, so as to provide for an input which is used during auto-scan.

FIG. 16 illustrates the block diagram of the ST level computer which provides an output signal to control the galvanometer 406 to provide a write out of the ST level information. The ST level computer may be of the type described in Pat. application Ser. No. 271,548, filed on July 13, 1972, in the name of Donald anderson, and reference is made to this Patent Application for a fuller description of the ST level computer. Generally, the input ECG signals from either the first or second channel is selected by a switch 448 for input to filter 450. The filter 450 is designed to provide particular frequency filtering in accordance with the tape speed of either X60 or X120 and these tape speed signals are shown applied to the input signal filter 450.

After the input ECG signal has been filtered, it is coupled to a sampling and level measuring circuit 452 which also receives the tape speed inputs. In addition, a sample time delay control 454 adjusts the ST sample point from 20 to 100 milliseconds after the start of the S-wave. After a determination of the DC level of the ST segment by the sampling and level measuring circuit 452, this DC level is filtered by a low pass filter 456 which may have its time constant adjusted by a control 458 to change the response time between a minimum to a maximum number of beats. The output from the low pass filter 456 is applied to an ST level amplifier 460 which includes a zero adjust 462. The amplifier 460 provides an output signal to control the galvanometer to provide for a write out of the ST level on the trend chart.

The ST level computer may also include detectors for excessive ST elevation of ST depression in a similar manner to the detection of high and low heart rate in FIG. 15. Specifically, a pair of potentiometers 451 and 453, which are coupled between a reference potential and ground provide output reference voltages which are applied to comparator 455 and 457. An output signal from the low pass filter 456 representing the ST level is also applied to the comparators 455 and 457. When the ST level is either elevated or depressed beyond the preset levels adjusted by the potentiometers 451 and 453, the comparators 455 and 457 provide output signals to the playback decoder shown in FIG. 9. The outputs from the comparators 455 and 457 provide for the automatic control of the real time write out during the auto-scan cycle. The ST control signals may be applied through particular ones of the switches 86 through 96 which switches control which individual ones of the external inputs are used to control the real time write out during the auto-scan cycle.

The use of the specific event outputs from the heart rate trend computer and the ST level computer provide for much greater flexibility in the analysis of the ECG signals than previous ECG computers. Specifically, these event outputs permit real time write outs whenever the recorded heart rate exceeds upper and/or lower preselected levels or when the ST level exceeds preselected elevated and/or depressed levels. For example, with heart rate, the potentiometers may be adjusted to provide for the proper ranges that are to be investigated, such as typically, 100 to 180 beats per minute for the high rate commonly called tachycardia, and 30 to 60 beats per minute for the low rate commonly called bradycardia. This provides a great flexibility in the investigation of the condition of the ECG signals. With the ST level event outputs, the potentiometers may be adjusted so as to investigate deviations of the patient's ST level during physical or mental stress periods, as compared to non-stress periods. An example of the significance of ST level phenomenon, which might be investigated would be a ST level elevation due to Prinzmetle variant angina, which is a transient ST level condition due to lack of blood to the heart. This condition often results in symptoms of angina pectoris and normally those symptoms would be entered in the patient's log during the recording period.

The arrhythmia computer section of electrocardioscanner also provides information for display in the arrhythmia computer display portion 18 shown in FIG. 1 and shown in more detail in FIG. 17. The arrhythmia computer also provides output signals for use by the paper writer to control the digital writer 14 to provide numerical indication of arrhythmia information, and also to control event markers to provide information representative of arrhythmia information exceeding a preselected value. The front panel 18 includes two windows 464 and 466, each of which display numbers up to 999. The left window 464 displays a number or premature ventricular contracts (VE). The right window 466 displays a number of supra-ventricular ectopic beats (SVE). Each display may be controlled by control switch 48 to totalize either in a one hour or on a cumulative basis. In addition, control of the event markers may be provided so that an output event mark is produced only when the number of VEs or SVEs exceed predetermined selected number of such VEs or SVEs. These are controlled by the switches designated 46. A reset button 468 controls all of the displays to return to zero.

The arrhythmia computer may also be provided with additional switches to permit inclusion of the R wave amplitude and R wave width criteria as part of the analysis of VE ectopic beats. Specifically, switches 465 and 467 are provided for selecting such criteria as R wave amplitude and width. In addition, a switch 469 may also be provided to control the selection of prematurity as a criteria for analysis of the VE ectopic beats and any combination of these switches may be individually actuated as may be required for the individual analysis of the particular patient's ECG abnormalities. For example, not all ventricular extrasystoles or additional beats possess differentially widened R waves, enlarged amplitudes or sufficiently premature complexes so as to be distinguishable from normal complexes. Therefore, the provision of selecting the individual criteria permits removal of these which do not apply to a particular patient's abnormality.

In addition to the switches, a continuous control 471 provides for a QRS control in milliseconds to permit varying the width criteria for accomodating an extended range of normal versus wide complexes. For example, ventricular ectopic comlexes originating high in the ventricular septal region may possess R wave complexes only slightly wider than normal complexes. This may be 50 to 70 milliseconds versus the 30 to 45 milliseconds typical of most normal complexes. Conversely, so called normal complexes may be significantly widened due to medication effects or due to cardia abnormalities, such as bundle branch block. The QRS control 471 therefore provides a means for the operator of the ECG computer to tailor the width criteria to the individual patient's ECG idiosyncracies.

The activation of the prematurity switch 464 provides for a comparison of the R—R interval between each ECG complex against the running average of a particular quantity, such as 10 to 15 of preceding ECG complexes. This switch, therefore, provides for the recognition when the ECG complex is premature by a particular percentage.

The arrhythmia computer receives the input ECG data and displays the computed data on the front panel 18 shown in FIG. 17 and has the computed data digitally printed out on the trend chart as shown in FIG. 12. As described above, a typical trend chart shows the VE and SVE information immediately following the time marker. In addition, the event markers at the middle and bottom edge of the trend chart paper provides event marks when the VEs and the SVEs exceed preselected number of events per minute.

FIG. 18 illustrates a block diagram of the arrhythmia computer. The input ECG data is coupled to a filter 470 which also receives speed signals from the tapedeck representing the trend speeds of X120 and X60. The speed data and the ECG data are coupled from the filter into the remaining portion of the arrhythmia computer and with the input speed data used to control timing functions, since the speed of the tapedeck would affect the timing of the signals. The output signals from the filter 470 are coupled to a plurality of comparator devices 472 through 476 which perform their comparisons in a conventional manner. Generally the comparators 472, 474 and 476 establish a plurality of criteria to determine if the ECG information contains an arrhythmia.

In order for the system of FIG. 18 to provide an output representing an arrhythmia event, the ECG complex must meet at least one of the following criteria. The first optional criteria as controlled by the switch 467 is shown in FIG. 19 and specifically, provides for the QRS width to be greater than a predetermined width, for example, the QRS width may be greater than 80 milliseconds. This is shown in FIG. 19 where a normal ECG complex having a QRS width of approximately 40 milliseconds is followed by an abnormal ECG complex having a QRS width of greater than 80 milliseconds. The width adjustment is provided by a control 471. The comparator 474 provides output signals representing whether the QRS segment is either wide or not wide. Comparator 474 may consist of an "R" wave width measuring circuit which is a flip-flop that is triggered as the R wave rises and reset as it falls. The time duration of this flip-flop is compared using standard gates against a time standard such as a oneshot which is triggered as the "R" wave rises.

In addition to the width criteria, the analyzer of FIG. 18 also provides an amplitude criteria which is optional under the control of the switch 465. Specifically, the amplitude of the QRS segment either positive or negative, may have an increase of more than 25% as compared to the average QRS amplitudes which have preceded the ECG complex being analyzed. The comparator 472 stores the average number of positive and negative amplitudes of the QRS segments of the preceding 10 complexes and compares that with the latest ECG complex to produce an output signal when the ECG complex is ±25% greater than the preceding average. The comparator 472 constantly updates so that each complex is not counted as a VE, but only when it exceeds by a selected amount, the average of the preceding ten. An amplitude setting 484 is used to control the desired level by which the ECG complex must exceed the previous ten and ±25 is merely representative. Comparator 472 may consist of standard sample and hold circuits which hold the amplitude peak of an R wave in an analog memory circuit such as a capacitor. A value of 25% of this peak is divided down by resistors then supplied to standard comparators which measure any input value to the other input in excess of 25% of the reference input. FIG. 20 illustrates this second criteria and shows an average ECG complex having average positive and negative QRS portions, which average complex is then followed by two typical complexes which have excessive positive or negative going portions. The comparator 472 also produces an output signal when the ECG complex has a positive going QRS portion.

The third criteria may be at the option of the operator through the use of the switch 489, and this criteria is termed as prematurity. Specifically, the comparator 476 provides an output signal representaive of prematurity the average of a particular number of beats (such as 10 to 15) is followed by another beat in a shorter period than normal (such as less than 20%. Comparator 476 may consist of standard sample and hold circuits which hold an amplitude equal to the R to R time period in an analog memory circuit such as a capacitor. A value of 20% less than this amplitude is supplied to standard comparators which measure when the R to R time period of any succeeding wave is premature by the predetermined amount.

All three of these criteria are coupled through switches 465, 467 and 469 to an AND gate 488 and the switches determine the number of conditions which must be met before the AND gate provides an output. The output from the AND gate is coupled to a register 490 for storing the VEs and the output of the storage register 490 is provided to the printer and to the VE display 464. The output from the storage register 490 is controlled by a one hour timing signal from the time clock and with the information coupled to the display and printer controlled by a switch 48. The reset button 468 provides reset to zero at any time. The AND gate 488 also is coupled through an event counter 492 which is controlled by one of a pair of switches 46 to provide an event output when the number of VEs per minute exceeds a predetermined number.

In addition to the output signals described above, each one of the individual characteristics may be used as a signal representing an unusual event so as to control a real time write out during the auto-scan cycle. For example, as shown in FIG. 18, the output from comparator 472 may be supplied as a high amplitude event signal. The output from comparator 474 may be suppled as a wide R wave signal. The output from comparator 476 may be supplied as a premature R wave signal. In addition, the output from "and" gate 488 which is also an input to the storage register 490, may be supplied as a signal representing a single VE. The output from the counter 492 may be supplied as a signal representing VE activity. Any one of these signals, or all of them, could be coupled through individual ones of switches such as switches 86 through 96 so as to control real time write out during the auto-scan cycle. In particular, the output signal from the "and" gate 488 is coupled through switch 86 and the output from counter 492 is coupled through switch 88 as two specific examples, but as indicated above, any number of switches may be used so as to control the particular activity which is desired to provide for a real time write out during the auto-scan cycle.

In order for an ECG complex to be counted as an SVE, three criteria must be met which are established by the comparators 472, 474 and 476.

As a first criteria, the output from the comparator 472 representing a positive going QRS must be present and as a second criteria a width of less than 80 milliseconds for the R wave must be provided by the comparator 474. As a third criteria, a signal representing prematurity must be present as described above and such a signal is provided from the comparator 476. The outputs from the comparators 472, 474 and 476 are coupled to an AND gate 494, and when all three inputs coincide, the AND gate 494 produces an output signal representative of an SVE.

This SVE output signal is coupled to a storage register 496 to store information in a similar manner to the storage register 490 and with the storage register controlled by either the manual reset 468, or the reset provided by the one hour time signal as controlled by switch 48. The output from the storage register 496 is coupled to the SVE digital display 466 and to the printer for printing on the paper chart the number of such SVEs on an hour-by-hour basis. The output from the AND gate is also coupled to an event counter 498 which provides control of the event marker to indicate when the number of SVEs per minute have exceeded a predetermined amount as selected by switch 46.

In addition to the output signals indicated above, representing various SVE conditions, individual ones of these conditions may be used to provide for individual signals to control the real time write out during auto-scan in accordance with individual characteristics. For example, the output from gate 494, which is also the input to event counter 498, may be provided as a signal representing a single SVE event. In addition, an output signal from the event counter 498 may be provided as a signal representing SVE activity.

In addition to the VE and SVE detection, as indicated above, the arrhythmia computer FIG. 18 may also include a paired beat detector 473 which receives as its input a signal from the filter 470 which represents detection of an R wave, and also a signal from the "and" gate 488, which represents the detection of a VE event. The output of the paired beat detector 473 may also be sent as an individual event signal to control the real time write out during auto-scan, and specifically would then provide for real time write outs of paired ectopic events. This may be important since it has been noted by several researchers that the mortality rate is significantly higher for patients with this characteristic, as compared to single ectopic beat episodes.

FIG. 18(a) illustrates a block diagram of a system for detecting paired beats and FIG. 18(b) shows wave forms explaining the operation of the paired beat detector. The paired beat output signal occurs only once for each episode of successive ectopic complexes. The detection begins with the recognition of the first pair of ectopic beats and terminates with the recognition of the first normal complex after the pair of ectopic beat. The R wave pulse is applied to a bistable multivibrator flip-flop 475 as the clock input. The signal representing the single VE ectopic beat is applied to the data input of the flip-flop 475, so that in the event a VE ectopic beat is detected, a logic "1" level is clocked to the "Q" output at the termination of the R wave pulse. Thus, any VE ectopic beat results in the "Q" output of the flip-flop 475 going from a logic "0" to a logic "1" level. A flip-flop 477 also receives as inputs the signal representing the VE ectopic beat and the R wave at the data and clock inputs, and when the "Q" output of flip-flop 475 goes to a logic "1" level this removes the inhibiting signal from the reset input of flip-flop 477. Therefore, in the event the following ECG complex is also analyzed as a VE ectopic beat, the R wave pulse clocks the "Q" output of the flip-flop 477 from a logic "0" to a logic "1" state, thus, indicating that two or more VE ectopic beats have occurred successfully. Both flip-flops 475 and 477 remain in their respective states until an ECG complex is not analyzed as a VE ectopic beat, at which time flip-flop 475 is clocked back to a logic "0" state thus resetting flip-flop 477 to the logic "0" state.

The reset switch 48 controls the storage registers 490 and 496 so that with the switch in the one hour position, ectopic beats or either VE or SVE are displayed as they occur continuously on the VE and SVE displays 464 and 466. However, at the end of each hour, the presentations are reset to zero. When the switch 48 is placed in the total position, ectopic beats are displayed as they occur, but with the display cumulative and continuously totaled without zeroing at the start of each hour. It is to be appreciated that the storage registers 490 and 496 may actually store the number of ectopic beats continuously even though the registers are zeroed so that by switching from the one hour position to the total position, the displays may provide the cumulative number of beats at any time. The printer 14 which provides the digital print out of the ectopic beats, provides the number of such beats for each hour and may either be controlled to provide such print out on an hour-by-hour basis or a cumulative basis.

As indicated above, the event per minute switches 46 select the maximum rate per minute occurrence of the ectopic beats beyond which the VE and SVE event markers will mark the chart paper as shown in FIG. 12. For example, if the event per minute switch 46 is set at thre, and three or more VEs occur within a minute, the event marker 402 shown in FIG. 14 will mark the chart, as shown in FIG. 13, to provide a mark of the event.

The final module shown in the front panel of FIG. 1 is the heartbeat computer 20, and this computer is shown in more detail in FIG. 21. Specifically, the heartbeat computer provides the number of heartbeats recorded on the original recording tape and these heartbeats can be totalized either on an hour-by-hour basis, or on a cumulative basis. This hour-by-hour or cumulative heartbeat data can be displayed using a plurality of display indicators 500, 502, up to any additional number of indicators. The display 504 is shown to be the last display. The heartbeat counter is used to count, in a bidirectional mode, the total number of heartbeats so that an exact ECG complex may be located at any given time. For example, a specific number relating to a particular ECG complex is located by viewing the tape at the slow speed and then observing the heartbeat counter number corresponding to the particular complex. After any further viewing or playing at high speed or even in the fast forward or fast reverse mode, the particular complex can be located by the particular heartbeat counter number.

In FIG. 21, the trigger input from FIG. 8 is applied to the system and since the trigger input corresponds to the R wave in each ECG complex, a single pulse output is provided for each complex. This single pulse for each complex occurs no matter whether the tape transport is moved in any of its speeds, such as X1, X30, X60 or X120, or in the Fast Forward or Fast Reverse modes. The trigger input is coupled to a plurality of bidirectional counter 506, 508 and up to any additional number of counter. The final bidirectional counter is shown as number 510. The counter provide the output signals for the displays 500, 502 and 504. The number of displays correspond in number to the number of counters. Each counter also has an input from the tapedeck when in the fast reverse mode, so that the counter provides for the subtraction of the pulses rather than an addition. A one hour time mark from the clock system is inputted into the counters so as to provide for total heartbeats on an hour-by-hour basis. The one hour time mark has also been shown to be used to provide for controlling information either into a display or into the printer. The displays may be of the type which includes a latch so that the information is maintained until reset or until the next one hour time signal, or the displays can provide a continuous output showing the total number of heartbeats.

The present invention as described above provides for a multispeed ECG scanning device which analyzes ECG complexes to provide outputs of such ECG complexes either in real time, in high speed playback with superimposition of two channels of ECG information, or with high speed playback with trend write out of heart rate and ST level and with automatic write out at real time ECG signals in accordance with predetermined events. The system is controlled by a digital clock driven by the movement of the tape, and provides the number of VEs and SVEs either on an hour-by-hour or total basis, and provides variable control to speeds and time base of the above factors.

Although the invention has been described with reference to a particular embodiment, it is to be appreciated that other variations and adaptations may be made and the invention is only to be limited by the appended claims.

We claim:

1. A dynamic multispeed ECG computer for reproducing ECG information contained on a recording medium recorded at a particular speed, including:

first means for moving the recording medium past at least one fixed predetermined real time readout position and at least one fixed predetermined high speed readout position, second means coupled to the first means for controlling the first means to move the recording medium at a selected one of a plurality of speeds including the particular speed and including more than one speed appreciably greater than the particular speed, to provide real time and high speed playbacks respectively of the recorded information, third means located at the fixed predetermined high speed readout position for reproducing the recorded information when the first means moves the recording medium to provide high speed playback, fourth means located at the fixed predetermined real time readout position for reproducing the recorded information when the first means moves the recording medium to provide real time playback, fifth means coupled to the third means and responsive to the reproduced signals at high speed playback for producing output signals in accordance with the trend of particular characteristics of the ECG complexes at high speed playback, sixth means coupled to the third means and responsive to the reproduced signals for producing control signals indicative of the occurrence of the predetermined events within the characteristics of the ECG complexes, and seventh means coupled to the sixth means and the second means and responsive to the control signals provided by the sixth means for controlling the second means to move the recording medium at the real time playback speed upon the occurrence of the predetermined events within the characteristics of the ECG complexes.

2. The ECG computer of claim 1 additionally including eighth means including a paper writer for reproducing the trend output signals and the paper writer operating at a speed to reproduce the trend output signals on a portion of the paper chart having a length equal to small fraction of the length of recording medium, and for reproducing the ECG signals and the paper writer operating at a speed to reproduce the ECG signals on a portion of the paper chart on a real time basis.

3. The ECG computer of claim 2 wherein the fifth means produces trend output signals representing heart beat rate and ST level and wherein the paper writer provides a two channel writeout of the trend information on the trend chart.

4. The ECG computer of claim 2 additionally including ninth means for producing a digital printout of time related to the time of recording of the ECG signals on a real time basis.

5. The ECG computer of claim 1 wherein the sixth means is responsive to the ectopic beats in the ECG information reproduced at high speed playback for producing the control signals.

6. The ECG computer of claim 1 wherein the sixth means is responsive to VE ectopic beats in the ECG information for producing the control signals.

7. The ECG computer of claim 1 wherein the sixth means is responsive to SVE ectopic beats in the ECG information for producing the control signals.

8. The ECG computer of claim 1 wherein the sixth means is responsive to a number of ectopic beats in the ECG information exceeding a predetermined number in a predetermined unit time for producing the control signals.

9. The ECG computer of claim 1 wherein the sixth means is responsive to a number of VE ectopic beats in the ECG information exceeding a predetermined number in a predetermined unit time for producing the control signals.

10. The ECG computer of claim 1 wherein the sixth means is responsive to a number of SVE ectopic beats in the ECG information exceeding a predetermined number in a predetermined unit time for producing the control signals.

11. The ECG computer of claim 1 wherein the sixth means is responsive to the amplitude of the R-wave component of the ECG information exceeding a predetermined quantity for producing the control signals.

12. The ECG computer of claim 1 wherein the sixth means is responsive to the width of the R-wave component of the ECG information exceeding a predetermined quantity for producing the control signals.

13. The ECG computer of claim 1 wherein the sixth means is responsive to the premature appearance of the R-wave component of the ECG information by a predetermined amount for producing the control signals.

14. The ECG computer of claim 1 wherein the sixth means is responsive to paired ectopic beats in the ECG information for producing the control signals.

15. The ECG computer of claim 1 wherein the sixth means is responsive to a heart beat rate of the ECG information exceeding a predetermined rate for producing the control signals.

16. The ECG computer of claim 1 wherein the sixth means is responsive to a heart beat rate of the ECG information lower than a predetermined rate for producing the control signals.

17. The ECG computer of claim 1 wherein the sixth means is responsive to an elevation of the ST level of the ECG information greater than a predetermined level for producing the control signals.

18. The ECG computer of claim 1 wherein the sixth means is responsive to a depressing of the ST level of the ECG information below a predetermined level for producing the control signals.

19. The ECG computer of claim 1 wherein the ECG information contained on the recording medium also contains event markers which have been recorded in accordance with the actuation of an event marking system by the patient and wherein the sixth means is responsive to the event markers in the ECG information for producing the control signals.

20. The ECG computer of claim 19 wherein the event marker consists of a short burst of pulses and wherein the sixth means detects such short burst of pulses.

21. The ECG computer of claim 20 wherein the short burst of pulses consists of a predetermined number of pulses in a predetermined period of time and wherein the sixth means includes means for detecting the predetermined number of pulses in the predetermined period of time.

22. The ECG computer of claim 1 additionally including eighth means coupled to the sixth means for inhibiting the sixth means for a first run of the recording medium at high speed to produce continuous trend outut signals from the beginning to the end of the recording medium and for cycling the recording medium back to the beginning and for enabling the sixth means for a second run of the recording medium from the beginning to the end.

23. An arrhythmia computer for use in a dynamic multispeed ECG computer for reproducing ECG information contained on a recording medium recorded at a particular speed, including:

first means for moving the recording medium past a fixed predetermined readout position, second means coupled to the first means for controlling the first means to move the recording medium at at least one selected speed appreciably greater than the particular speed to provide high speed playback of the recorded information, third means located at the fixed predetermined readout position for reproducing the recorded information when the first means moves the recording medium to provide the high speed playback, fourth means coupled to the third means and responsive to the reproduced information for detecting the presence of ectopic beats within the reproduced information in accordance with parameters selectable singly and in combinations and including the amplitude, width and prematurity of the R-wave portion of the ECG complexes within the ECG information, and fifth means coupled to the fourth means for selecting singly and in combinations the parameters used as a basis for detecting the presence of ectopic beats.

24. The arrhythmia computer for use in the ECG computer of claim 23 additionally including sixth means coupled to the fourth means for varying the width parameter within a preselected range.

25. The arrhythmia computer for use in the ECG computer of claim 23 additionally including sixth means coupled to the fourth and fifth means for producing individual control signals in accordance with each of the individual parameters and a control signal in accordance with the selected combination of parameters.

26. The arrhythmia computer for use in the ECG computer of claim 23 wherein the fifth means provides for the individual selection of parameters for controlling the detection of VE ectopic beats and wherein the fourth means provides for preselected parameters controlling the detection of SVE ectopic beats.

27. The arrhythmia computer for use in the ECG computer of claim 26 additionally including sixth means coupled to the fourth and fifth means for producing individual control signals in accordance with each of the individual parameters and individual control signals in accordance with the selected combination of parameters for detecting VE ectopic beats and with the preselected parameters for detecting SVE ectopic beats.

28. The arrhythmia computer for use in the ECG computer of claim 27 additionally including seventh means coupled to the sixth means for producing individual control signals in accordance with a preselected activity of detected VE and SVE beats.

29. The arrhythmia computer for use in the ECG computer of claim 23 additionally including sixth means coupled to the fourth means for detecting the presence of paired ectopic beats.

30. The arrhythmia computer for use in the ECG computer of claim 29 additionally including seventh means coupled to the sixth means for producing a control signal in accordance with the detection of paired ectopic beats.

[31. A recorder for use with a dynamic multispeed ECG computer for reproducing ECG information contained on a recording medium recorded at a particular speed and with the ECG computer including first means for moving the recording medium past a plurality of fixed predetermined readout positions and with the ECG computer including second means for controlling the first means to move the recording medium at a selected one of a plurality of speeds including the particular speed and including at least one speed appreciably greater than the particular speed, to provide real time and high speed playbacks respectively of the recorded information and with the ECG computer including third means located at a first one of the fixed predetermined readout positions for reproducing the recorded information when the first means moves the recording medium to provide real time playback and with the ECG computer including fourth means located at a second one of the fixed predetermined readout positions for reproducing the recorded information when the first means moves the recording medium to provide high speed playback and with the ECG computer including fifth means responsive to an event signal contained within the ECG information played back at high speed to control the second means to move the recording medium for real time playback for a predetermined period of time and then control the second means to return to a high speed playback, the recorder including:

a recording medium system for recording ECG information in response to input signals, an event marker for producing an event signal, and switching means coupled to the event marker and the recording medium system for controlling the recording of the event signal on the recording medium in response to the actuation of the switching means.]

[32. The recorder of claim 31 wherein the event signal consists of a short burst of pulses.]

[33. The recorder of claim 32 wherein the short burst of pulses consists of a predetermined number of pulses in a predetermined period of time.]

34. A dynamic multispeed ECG computer for reproducing ECG information contained on a recording medium recorded at a particular speed, including:

first means for moving the recording medium past a plurality of fixed predetermined readout positions, second means coupled to the first means for controlling the first means to move the recording medium at a selected one of a plurality of speeds including the particular speed of recording and including more than one speed appreciably greater than the particular speed to provide real time and high speed playbacks respectively of the recorded information, third means located at a first one of the fixed predetermined readout positions for reproducing the recorded information when the first means moves the recording medium to provide real time playback, fourth means located at a second one of the fixed predetermined readout positions for reproducing the recorded information when the first means moves the recording medium to provide high speed playback, fifth means coupled to the fourth means and responsive to the reproduced signals at high speed playback for producing output signals in accordance with the trend of particular characteristics of the ECG complexes at high speed playback, sixth means coupled to the fourth means and responsive to the reproduced signals for producing control signals upon the detection of predetermined characteristics of the ECG complexes, seventh means coupled to the sixth means and the second means and responsive to the control signals produced by the sixth means for controlling the second means to move the recording medium at the real time playback speed for a predetermined period of time upon the detection of the predetermined characteristis of the ECG complexes and to then return to the selected one of the multispeed high speed playbacks, and eighth means coupled to the fifth, sixth and seventh means for inhibiting the production of the control signals by the sixth means during a first forward run of the recording medium from the beginning to the end to provide a continuous high speed trend output, for immediately rewinding the recording medium to the beginnning, and for then enabling the production of the control signals by said sixth means during a second forward run of the recording medium from the beginning to the end in which the recording medium is run at the real time playback speed for a predetermined period of time upon the detection of the predetermined characteristics of the ECG complexes under control of said seventh means.

35. The ECG computer of claim 34 additionally including ninth means including a paper writer for reproducing the trend output signals and the paper writer operating at a speed to reproduce the trend output signals on a portion of the paper chart having a length equal to a small fraction of the length of recording medium, and for reproducing the ECG signals and the paper writer operating at a speed to reproduce the ECG signals on a portion of the paper chart on a real time basis.

36. The ECG computer of claim 35 wherein the fifth means produces trend output signals representing heart beat rate and ST level and wherein the paper writer provides a two channel writeout of the trend information on the trend chart.

37. The ECG computer of claim 35 additionally including tenth means for producing a digital printout of time related to the time of recording of the ECG signals on a real time basis.

38. The ECG computer of claim 35 wherein the sixth means is responsive to ectopic beats in the ECG information reproduced at high speed playback for producing the control signals.

39. The ECG computer of claim 34 wherein the sixth means is responsive to VE ectopic beats in the ECG information for producing the control signals.

40. The ECG computer of claim 34 wherein the sixth means is responsive to SVE ectopic beats in the ECG information for producing the control signals.

41. The ECG computer of claim 34 wherein the sixth means is responsive to a number of ectopic beats in the ECG information exceeding a predetermined number in a predetermined unit time for producing the control signals.

42. The ECG computer of claim 34 wherein the sixth means is responsive to a number of VE ectopic beats in the ECG information exceeding a predetermined number in a predetermined unit time for producing the control signals.

43. The ECG computer of claim 34 wherein the sixth means is responsive to a number of SVE ectopic beats in the ECG information exceeding a predetermined number in a predetermined unit time for producing the control signals.

44. The ECG computer of claim 34 wherein the sixth means is responsive to the amplitude of the R-wave component of the ECG information exceeding a predetermined quantity for producing the control signals.

45. The ECG computer of claim 34 wherein the sixth means is responsive to the width of the R-wave component of the ECG information exceeding a predetermined quantity for producing the control signals.

46. The ECG computer of claim 34 wherein the sixth means is responsive to the premature appearance of the R-wave component of the ECG information by a predetermined amount for producing the control signals.

47. The ECG computer of claim 34 wherein the sixth means is responsive to paired ectopic beats in the ECG information for producing the control switches.

48. The ECG computer of claim 34 wherein the sixth means is responsive to a heart beat rate of the ECG information exceeding a predetermined rate for producing the control signals.

49. The ECG computer of claim 34 wherein the sixth means is responsive to a heart beat rate of the ECG information lower than a predetermined rate for producing the control signals.

50. The ECG computer of claim 34 wherein the sixth means is responsive to an elevation of the ST level of the ECG information greater than a predetermined level for producing the control signals.

51. The ECG computer of claim 34 wherein the sixth means is responsive to a depressing of the ST level of the ECG information below a predetermined level for producing the control signals.

52. The ECG computer of claim 34 wherein the ECG information contained on the recording medium also contains event markers which have been recorded in accordance with the actuation of an event marking system by the patient and wherein the sixth means is responsive to the event markers in the ECG information for producing the control signals.

53. The ECG computer of claim 52 wherein the event marker consists of a short burst of pulses and wherein the sixth means detects such short burst of pulses.

54. The ECG computer of claim 53 wherein the short burst of pulses consists of a predetermined number of pulses in a predetermined period of time and wherein the sixth means includes means for detecting the predetermined number of pulses in the predetermined period of time.

55. In a dynamic multispeed ECG computer for reproducing ECG information contained on a recording medium recorded at a particular speed, including a first means for moving the recording medium at at least one fixed predetermined real time readout position and at least one fixed predetermined high speed readout position, a second means coupled to the first means for controlling the first means to move the recording medium at a selected one of a plurality of speeds including the particular speed and including more than one speed appreciably greater than the particular speed to provide real time and high speed playbacks respectively of the recorded information, a third means located at the fixed predetermined high speed readoutposition for reproducing the recorded information when the first means moves the recording medium to provide high speed playback, a fourth means located at the fixed predetermined real time readout position for reproducing the recorded information when the first means moves the recording medium to provide real time playback, a fifth means coupled to the third means and responsive to the reproduced signals at high speed playback for producing output signals in accordance with the trend of particular characteristics of the ECG complexes at high speed playback, and a sixth means coupled to the third means and responsive to the reproduced signals for producing control signals indicative of the occurrence of the predetermined events within the characteristics of the ECG complexes, the improvement comprising:

seventh means coupled to the sixth means and the second means and responsive to the control signals provided by the sixth means for controlling the second means to move the recording medium at the real time playback speed upon the occurrence of the predetermined events within the characteristics of the ECG complexes.

56. In an arrhythmia computer for use in a dynamic multispeed ECG computer for reproducing ECG information contained on a recording medium recorded at a particular speed and including a first means for moving the recording medium past a fixed predetermined readout position, a second means coupled to the first means for controlling the first means to move the recording medium at at least one selected speed appreciably greater than the particular speed to provide high speed playback of the recorded information, a third means located at the fixed predetermined readout position for reproducing the recorded information when the first means moves the recording medium to provide the high speed playback, the improvement comprising:

fourth means coupled to the third means and responsive to the reproduced information for detecting the presence of ectopic beats within the reproduced information in accordance with parameters selectable singly and in combinations and including the amplitude, width and prematurity of the R-wave portion of the ECG complexes within the ECG information, and, fifth means coupled to the fourth means for selecting singly and in combinations the parameters used as a basis for detecting the presence of ectopic beats.

57. In a dynamic multispeed ECG computer for reproducing ECG information contained on a recording medium recorded at a particular speed and including a first means for moving the recording medium past a plurality of fixed predetermined readout positions, a second means coupled to the first means for controlling the first means to move the recording medium at a selected one of a plurality of speeds including the particular speed of recording and including more than one speed appreciably greater than the the particular speed to provide real time and high speed playbacks respectively of the recorded information, a third means located at a first one of the fixed predetermined readout positions for reproducing the recorded information when the first means moves the recording medium to provide real time playback, a fourth means located at a second one of the fixed predetermined readout positions for reproducing the recorded informatin when the first means moves the recording medium to provide high speed playback, a fifth means coupled to the fourth means and responsive to the reproduced signals at high speed playback for producing output signals in accordance with the trend of particular characteristics of the ECG complexes past high speed playback, a sixth means coupled to the fourth means and responsive to the reproduced signals for producing control signals upon detection of predetermined characteristics of the ECG complexes, the improvement comprising:

seventh means coupled to the sixth means and the second means and responsive to the control signals produced by the sixth means for controlling the second means to move the recording medium at the real time playback speed for a predetermined period of time upon the detection of the predetermined characteristics of the ECT complexes and to then return to the selected one of the multispeed high speed playbacks, and, eighth means coupled to the fifth, sixth and seventh means for inhibiting the production of the control signals by the sixth means during a first forward run of the recording medium from the beginning to the end to provide a continuous high speed trend output, for immediately rewinding the recording medium to the beginning, and for then enabling the productin of the control signals by the sixth means during a second forward run of the recording medium from the beginning to the end in which the recording medium is run at the real time playback speed for a predetermined period of time upon the detection of the predetermined characteristics of the ECG complexes under control of said seventh means.

* * * * *